US012636352B2

(12) United States Patent     (10) Patent No.:   US 12,636,352 B2

Sañchez Ordoñez et al.     (45) Date of Patent:    May 26, 2026

---

(54) FUNCTIONALIZED ENZYME-POWERED NANOMOTORS

(71) Applicants: FUNDACIO INSTITUT DE BIOENGINYERIA DE CATALUNYA, Barcelona (ES); INSTITUCIO CATALANA DE RECERCA I ESTUDIS AVANÇATS, Barcelona (ES)

(72) Inventors: Samuel Sañchez Ordoñez, Barcelona (ES); Tania Patiño Padial, Barcelona (ES); Ana Candida Lopes Hortelão, Barcelona (ES)

(73) Assignees: FUNDACIO INSTITUT DE BIOENGINYERIA DE CATALUNYA, Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 343 days.

(21) Appl. No.: 17/299,727

(22) PCT Filed: Dec. 4, 2019

(86) PCT No.: PCT/EP2019/083662
§ 371 (c)(1),
(2) Date: Jun. 3, 2021

(87) PCT Pub. No.: WO2020/115124
PCT Pub. Date: Jun. 11, 2020

(65) Prior Publication Data
US 2022/0016223 A1    Jan. 20, 2022

(30) Foreign Application Priority Data

Dec. 5, 2018   (EP) ..................................... 18382896

(51) Int. Cl.
*A61K 38/50*     (2006.01)
*A61K 47/69*     (2017.01)
(Continued)

(52) U.S. Cl.
CPC .............. *A61K 38/50* (2013.01); *B82Y 15/00* (2013.01); *C12N 9/80* (2013.01); *G01N 33/582* (2013.01);
(Continued)

(58) Field of Classification Search
CPC ...................................................... A61K 38/50
See application file for complete search history.

(56) References Cited

U.S. PATENT DOCUMENTS

2013/0084569 A1*   4/2013   Wang ..................... B01D 61/00
                                                   977/773
2016/0243254 A1*   8/2016   Artzi .................. A61K 49/0093
2018/0134549 A1*   5/2018   Le ........................... B82Y 5/00

OTHER PUBLICATIONS

Wu et al. "Self-Propelled Polymer Multilayer Janus Capsules for Effective DrugDelivery and Light-Triggered Release", ACS Appl. Mater. Interfaces 2014, 6, 10476-10481 (Year: 2014).*
(Continued)

*Primary Examiner* — Isaac Shomer
(74) *Attorney, Agent, or Firm* — Chrisman Gallo Tochtrop LLC

(57) ABSTRACT

The present invention provides an enzyme-powered nanomotor, comprising a particle with a surface, an enzyme, and a heterologous molecule; characterized in that the enzyme and the heterologous molecule are discontinuously attached over the whole surface of the particle. The invention also provides the nanomotor for use in therapy, diagnosis and prognosis, in particular, for the treatment of cancer. Addi-
(Continued)

A tionally, the invention provides the use of the nanomotor for detecting an analyte in an isolated sample.

15 Claims, 5 Drawing Sheets

Specification includes a Sequence Listing.

(51) Int. Cl.

| | |
|---|---|
| B82Y 5/00 | (2011.01) |
| B82Y 15/00 | (2011.01) |
| B82Y 30/00 | (2011.01) |
| B82Y 35/00 | (2011.01) |
| B82Y 40/00 | (2011.01) |
| C12N 9/80 | (2006.01) |
| G01N 33/58 | (2006.01) |
| A61K 47/60 | (2017.01) |
| A61K 47/68 | (2017.01) |

(52) U.S. Cl.
CPC .......... *A61K 47/60* (2017.08); *A61K 47/6861* (2017.08); *A61K 47/6929* (2017.08); *B82Y 5/00* (2013.01); *B82Y 30/00* (2013.01); *B82Y 35/00* (2013.01); *B82Y 40/00* (2013.01); *C01P 2004/03* (2013.01); *C01P 2004/50* (2013.01); *C01P 2004/64* (2013.01); *C12Y 305/01005* (2013.01)

(56) References Cited

OTHER PUBLICATIONS

Pai Peng, Lili Shi, Huihui Wang and Tao Li. "A DNA nanoswitch-controlled reversible nanosensor." Nucleic Acids Research, vol. 45, No. 2, pp. 541-546, published online Nov. 28, 2016 (Year: 2016).*

Xing Ma et al. "Enzyme-Powered Hollow Mesoporous Janus Nanomotors." Nano Letters, vol. 15, 2015, pp. 7043-7050 and S1-S14. (Year: 2015).*

Ana C. Hortelão, Tania Patiño, Ariadna Perez-Jiménez, Àngel Blanco, and Samuel Sánchez. "Enzyme-Powered Nanobots Enhance Anticancer Drug Delivery." Advanced Functional Materials, vol. 28, 2018, 1705086, pp. 1-10 and supplemental pp. 1-3, published Nov. 27, 2017. (Year: 2017).*

Daniel A. Richards, Antoine Maruani and Vijay Chudasama. "Antibody fragments as nanoparticle targeting ligands: a step in the right direction." Chemical Science, vol. 8, 2017, pp. 63-77. (Year: 2017).*

Tania Patiño et al. "Influence of Enzyme Quantity and Distribution on the Self-Propulsion of Non-Janus Urease-Powered Micromotors." Journal of the American Chemical Society, vol. 140, 2018, pp. 7896-7903 and S1-S9, published May 22, 2018. (Year: 2018).*

Micromotors Powered by Enzyme Catalysis Krishna K. Dey, Xi Zhao, Benjamin M. Tansi, Wilfredo J. Méndez-Ortiz, Ubaldo M. Córdova-Figueroa, Ramin Golestanian, and Ayusman Sen Nano Letters 2015 15 (12), 8311-8315.

Motion Control of Urea-Powered Biocompatible Hollow Microcapsules Xing Ma, Xu Wang, Kersten Hahn, and Samuel Sánchez ACS Nano 2016 10 (3), 3597-3605 DOI: 10.1021/acsnano.5b08067.

Enzyme-Powered Nanobots Enhance Anticancer Drug Delivery Hortelão, A. C., Patiño, T., Perez-Jiménez, A., Blanco, À., Sánchez, S., Adv. Funct. Mater. 2018, 28, 1705086.

Patiño T, Feiner-Gracia N, Arqué X, Miguel-López A, Jannasch A, Stumpp T, Schäffer E, Albertazzi L, Sánchez S. Influence of Enzyme Quantity and Distribution on the Self-Propulsion of Non-Janus Urease-Powered Micromotors. J Am Chem Soc. Jun. 27, 2018;140(25):7896-7903. doi: 10.1021/jacs.8b03460. Epub May 29, 2018. PMID: 29786426.

Campuzano S, Kagan D, Orozco J, Wang J. Motion-driven sensing and biosensing using electrochemically propelled nanomotors. Analyst. Nov. 21, 2011;136(22):4621-30. doi: 10.1039/c1an15599g. Epub Sep. 14, 2011. PMID: 21915400.

Altschul SF, Gish W, Miller W, Myers EW, Lipman DJ. Basic local alignment search tool. J Mol Biol. Oct. 5, 1990;215(3):403-10. doi: 10.1016/S0022-2836(05)80360-2. PMID: 2231712.

Higgins DG, Bleasby AJ, Fuchs R. Clustal V: improved software for multiple sequence alignment. Comput Appl Biosci. Apr. 1992;8(2):189-91. doi: 10.1093/bioinformatics/8.2.189. PMID: 1591615.

Inman BA, Etienne W, Rubin R, Owusu RA, Oliveira TR, Rodriques DB, Maccarini PF, Stauffer PR, Mashal A, Dewhirst MW. The impact of temperature and urinary constituents on urine viscosity and its relevance to bladder hyperthermia treatment. Int J Hyperthermia. May 2013;29(3):206-10. doi: 10.3109/02656736.2013. 775355. Epub Mar. 14, 2013. PMID: 23489163.

Spectrophotometric and kinetics investigation of the Berthelot reaction for the determination of ammonia Charles J. Patton and S. R. Crouch Analytical Chemistry 1977 49 (3), 464-469 DOI: 10.1021/ac50011a034.

Rucinskaite, G., et al., "Enzyme-Coated Janus Nanoparticles That Selectively Bind Cell Receptors as a Function of the Concentration of Glucose", Nanoscale, (2017), 4;9(17):5404-5407; DOI: 10.1039/C7NR00298J.

Patiño, T., et al., "Influence of enzyme quantity and distribution on the self-propulsion of non-Janus urease powered micromotors", J. Am. Chem. Soc., (2018), 140(25):7896-7903; DOI: 10.1021/jacs. 8b03460.

\* cited by examiner

A

A                                          B

| | Cy3 Fluorescence Intensity within Spheroids (a.u.) | | Proliferation (%) | |
|---|---|---|---|---|
| Urea Concentration (mM) | 0 | 40 | 0 mM | 40 mM |
| MSNP-Ur/PEG | 1.51E+06 ± 2.27E+05 | 4.80E+06 ±4.78E+05 | 94.9 ± 3.4 | 76.6 ± 6.0 |
| MSNP-Ur/PEG-Ab | 6.67E+06 ± 4.56E+06 | 2.08E+07 ± 4.04E06 | 67.9 ± 2.1 | 53.9 ±2.9 |

SEQUENCE LISTING

```
<160> NUMBER OF SEQ ID NOS: 3

<210> SEQ ID NO 1
<211> LENGTH: 65
<212> TYPE: DNA
<213> ORGANISM: artificial
<220> FEATURE:
<223> OTHER INFORMATION: nanoswitch

<400> SEQUENCE: 1
tccttgtctg tctgtctgtc ttttttgaag aaggaattta ttccttcttc gtttgcttct      60
tcctt                                                                  65

<210> SEQ ID NO 2
<211> LENGTH: 20
<212> TYPE: DNA
<213> ORGANISM: artificial
<220> FEATURE:
<223> OTHER INFORMATION: scaffold
<220> FEATURE:
<221> NAME/KEY: modified_base
<222> LOCATION: (20)..(20)
<223> OTHER INFORMATION: AMIDATION

<400> SEQUENCE: 2
gacagacaga cagacaagga                                                  20

<210> SEQ ID NO 3
<211> LENGTH: 36
<212> TYPE: DNA
<213> ORGANISM: artificial
<220> FEATURE:
<223> OTHER INFORMATION: Control switch

<400> SEQUENCE: 3
tccttgtctg tctgtctgtc tgaacgtttt tcgttc                                36
```

FUNCTIONALIZED ENZYME-POWERED NANOMOTORS

CROSS REFERENCE TO RELATED APPLICATION

This application is a U.S. National Phase of International Application No. PCT/EP2019/083662, filed Dec. 4, 2019, which claims priority to European Patent Application No. 18382896.1, filed Dec. 5, 2018, both of which are incorporated by reference herein in their entirety.

This application claims the benefit of European Patent Application EP18382896 filed on Dec. 5, 2018.

TECHNICAL FIELD

The present invention belongs to the field of nanotechnology. In particular, the invention relates to enzyme-powered nanomotors externally functionalized. The nanomotors of the invention are particularly useful for therapy and biosensing.

BACKGROUND ART

Catalytic microswimmers are artificial systems able to self-propel thanks to the conversion of chemical energy into a mechanical force which ultimately translates into active motion.

While chemically powered micro and nanomotors have shown promising applicability in many fields such as environmental remediation, cargo transport and delivery, tissue and cell penetration, and active drug delivery to the stomach in vivo, their implementation in biomedicine is often restricted by either the inherent toxicity of the fuel or its limited availability within the organism.

Recently, the use of enzyme catalysis has emerged as an attractive alternative to replace commonly used toxic fuels since it offers unique features including biocompatibility, versatility and fuel bioavailability. In this regard, the use of urease, catalase, and glucose oxidase has shown to increase the diffusion of nano-sized particles at physiologically relevant concentrations of the enzyme substrate.

In addition, a directional propulsion can be achieved when using urease to power hollow silica Janus particles—i.e. particles with two hemispheres in which only one of them is coupled to the enzyme. Their motion can be switched on and off by the addition of enzyme inhibiting salts and the trajectories can be modified on-demand by the application of a magnetic field, allowing a high degree of controllability (Xing M A et al., "Motion Control of Urea-Powered Biocompatible Hollow Microcapsules", ACS Nano., 2016, vol. 10(3), pp. 3597-605).

It has also been described the use of enzyme-propelled nanomotors to increase the delivery efficiency of doxorubicin to cancer cells in vitro (Ana C. et al., "Enzyme-Powered Nanobots Enhance Anticancer Drug Delivery", Advanced Functional Materials, 2017, vol. 28(25)).

However, production of spherical Janus particles involves expensive and time-consuming techniques that may compromise their scalability and, therefore, their applicability.

More recently, and despite the fact that an asymmetric structure and distribution of the catalyst has traditionally been claimed to be essential for the generation of active motion, it was shown the self-propulsion of non-Janus spherical motors powered by enzyme catalysis located over the whole particle surface (Patino T. et al., "Influence of Enzyme Quantity and Distribution on the Self-Propulsion of Non-Janus Urease-Powered Micromotors", J. Am. Chem. Soc., 2018, vol. 140(25), pp. 7896-7903). However, the movement of this type of nanomotors was shown to be extremely sensitive to the enzyme coverage. In fact, it was found that a large number of enzymes molecules per nanomotor was necessary to achieve the desired movement. This has strongly hindered the use and applicability of these nanomotors due to the limitations it imposes on external functionalization.

Therefore, despite of the efforts made so far, there is a still a need for enzyme-powered nanomotors that are easy to produce and to adapt to various applications while maintaining a high movement capacity.

SUMMARY OF INVENTION

The present inventors have developed novel enzyme-propelled functionalized nanomotors that are useful in a variety of biomedical, chemical and environmental applications.

Surprisingly, the inventors found that by externally attaching a molecule to enzyme-powered non-Janus nanomotors, they could maintain or even increase the velocity and movement patterns of the particles (see FIG. 2D and FIG. 7B).

This was highly unexpected since it was previously shown that nanomotors in which the propulsion enzymes are attached over the whole surface of the particle have a movement highly dependent on enzyme coverage. Therefore, when the number of enzymes drops below a given threshold, it was shown that the movement of the particle was completely abolished (Patino T. et al., supra). Hence, it was evident that any modification performed on the surface of these particles, which necessarily reduces the available surface for enzyme attachment, was expected to reduce the nanomotor movement capacity, and therefore, its applicability.

As shown in the examples below, the inventors have found that the external attachment of different types of voluminous molecules, such as antibodies or DNA structures, not only does not affect the movement of nanomotors, but it also increases their cell-penetration capacity, stability and avoids their aggregation. FIG. 4, shows the higher capacity of nanomotors functionalized with an antibody to penetrate tumoral cells despite of lacking any cell penetration peptides.

Additionally, the inventors surprisingly found that the functionalized enzyme-powered nanomotors provided herein present such a strong activity that they are able to increase cancer cell death even when they are not loaded with any cytotoxic drug (see FIG. 4D).

This constitutes a great advantage because it allows the development of anticancer treatments with higher specificity and lower secondary effects.

An important advantage of the nanomotors of the invention is their versatility-they can be engineered with different enzymes to make them active only in the locations where the substrate is present. This further provides the advantage of allowing the development of treatments with high specific and low secondary effects.

In view of the above, the nanomotors of the invention provide a very valuable tool useful in a variety of fields such as disease treatment and biosensing.

Thus, in a first aspect, the invention provides an enzyme-powered nanomotor, comprising a particle with a surface; an enzyme; and a heterologous molecule; characterized in that the enzyme and the heterologous molecule are discontinuously attached over the whole surface of the particle. The invention also provides an enzyme-powered nanomotor, comprising a particle with a surface; an enzyme; and a heterologous molecule; wherein the enzyme and the heterologous molecule are discontinuously attached over the whole surface of the particle.

In a second aspect, the invention provides, a pharmaceutical composition comprising a therapeutically effective amount of the nanomotor as defined in the first aspect, and a pharmaceutically acceptable excipient and/or carrier.

In a third aspect, the invention provides, the nanomotor as defined in the first aspect or the pharmaceutical composition as defined in the second aspect, for use in therapy, diagnosis or prognosis.

In a fourth aspect, the invention provides a kit of parts comprising a nanomotor as defined in the first aspect or the pharmaceutical composition as defined in the second aspect, and optionally, instructions for its use. The invention also provides a kit of parts comprising a nanomotor as defined in the first aspect or the pharmaceutical composition as defined in the second aspect and instructions for its use. The kit of the invention may further comprise a buffer suitable to dilute the nanomotors of the invention, or a buffer to resuspend the dried or lyophilized nanomotors of the invention.

In a fifth aspect, the invention provides an in vitro method of detecting an analyte in an isolated sample, which comprises contacting the nanomotor as defined the first aspect with the sample.

In a sixth aspect, the invention provides the use of the nanomotor as defined in the first aspect in an in vitro method for detecting an analyte in an isolated sample.

DETAILED DESCRIPTION OF THE INVENTION

Figure 1:
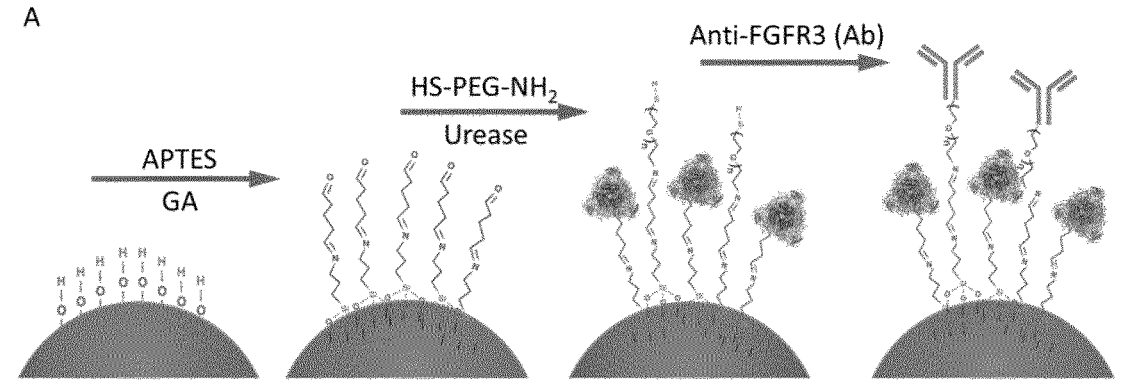
FIG. 1, related to Example 1, shows the fabrication and characterization of urease/PEG nanomotors (MSNP-Ur/PEG) and antibody-modified urease nanomotors (MSNP-Ur/PEG-Ab). A) Scheme illustrating the stepwise fabrication process to obtain the nanomotors.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

The term "enzyme-propelled nanomotor" or "enzyme-powered nanomotor" refers to a molecular device, on a micro or nano scale, capable of converting chemical energy into movement through the action of an enzyme located on the surface of the device. In other words, a nanomotor is a nanoparticle or a microparticle externally functionalized with enzymes. Without being bound by the theory, the enzymes generate movement through the asymmetric release of products involved in the catalytic reaction creating interfacial forces depending on osmotic gradients, charges, or other properties. The terms "nanomotor" and "micromotor" are used interchangeably in the present application.

As use herein, "heterologous molecule" refers to any molecule different from the enzyme(s), said enzyme(s) in charge of the propulsion of the nanomotor, and that is discontinuously attached over the whole surface of the particle. The embodiments thereby enable basically any type of molecule that can be linked to the particle to be immobilized onto a surface through its direct or indirect connection to the particle.

The below provided list of heterologous molecules should merely be seen as an illustrative and non-limiting list of molecules that could be used in the nanomotors of the invention. The embodiments are, however, not limited thereto and encompasses any heterologous molecule that can be linked directly or indirectly to a nanomotor of the embodiments.

The heterologous molecule of interest could be selected among markers, such as fluorescent markers, i.e. a fluorophore, e.g. fluorescein isothiocyanate (FITC), tetramethylrhodamine isothiocyanate (TRITC) and other isothiocyanates; N-hydroxysuccinimide (NHS) fluorescein and other succinimidyl esters; fluorescein-5-maleimide and other maleimide activated fluorophores; cyanine fluorophores; fluroescein fluorophores; rhodamine fluorophores; ATTO dyes; DyLight Fluor dyes; Alexa Fluor dyes; and borondipyrromethene (BODIPY) dyes. Further examples include isotope labels or markers, chemiluminescent markers, radiopaque markers, etc. In such a case, the nanomotor can be used as a test molecule to enable detection, using the marker, of the nanomotor on a surface.

Further examples of heterologous molecules include cell adhesion and cell attachment molecules, such cell adhesion molecules (CAMs), including immunoglobulin (Ig) superfamily, integrins, cadhereins and selectins.

A further example of a heterologous molecule is extracellular matrix (ECM) molecules including, for instance, proteoglycans (PGs), glycosaminoglycans (GAGs), heparan sulfate (HS), chondroitin sulfates, keratin sulfates, collagen, elastins, etc.

A related type of molecular of interest is basal lamina molecules that include molecules of the basal lamina, which is a layer of ECM secreted by epithelial cells. Non-limiting examples of such basal lamina molecules include laminin, type IV collagen, entactin and perlecan.

Yet another example of a heterologous molecule of interest is an anti-inflammatory molecule, such as corticosteroids; glucocorticoids; non-steroidal anti-inflammatory drugs (NSAIDs), such as acetylsalicylic acid, iso-butyl-propanoic-phenolic acid and naproxen sodium (INN); lipoxins; interleukin-1 receptor antagonist (IL-1 RA); etc.

Antibiotics can also be used as heterologous molecules of interest in order to inhibit bacterial growth or kill bacteria. Non-limiting examples of antibiotics include penicillins; cephalosporins; polymyxins; rifamycins; lipiarmycins; quinolones; sulfonamides; macrolides; lincosamides; tetracylines; bactericidal aminoglycosides; cyclic lipopeptides, such as daptomycin; glycylcylines, such as tigecycline; oxazolidones, such as linezolid; and lipiarmycins, such as fidaxomicin.

In a similar way molecules targeting other types of microbes, such as anti-fungal molecules, e.g. polyene anti-fungals, such as amphotericin B, candicidin, filipin, hamycin, natamycin, nystatin and rimocidin; azole anti-fungals, such as imidazoles, e.g. bifonazole, butoconazole, clotrimazole, econazole, fenticonazole, isoconazole, miconazole, omoconazole, oxiconazole, sertaconazole, sulconazole and tioconazole; triazoles, e.g. albaconazole, fluconazole, isavuconazole, itraconazole, posaconazole, ravuconazole, terconazole and voriconazole; and thiazoles, e.g. abafungin; allylamines, such as amorolfin, butenafine, naftifine and terbinafine; echinocandins, such as anidulafungin, caspofungin and micafungin; benzoic acid; ciclopirox olamine; flucytosine; griseofulvin; tolnaftate and undecylenic acid. Also anti-viral molecules, e.g. virus-assisted protein (VAP) anti-idiotypic antibodies; amantadine; rimantadine; pleconaril; acyclovir; zidovudine (AZT); lamivudine; integrase; fomivirsen; rifampicin; zanamivir and oseltamivir, and anti-parasitic molecules, such as mebendazole; pyrantel pamoate; thiabendazole; diethylcarbamazine; ivermectrin; niclosamide; praziquantel; albendazole; praziquantel; rifampin; amphotericin B; melarosprol; elfornithine; metronidazole; tinidazole and miltefosine, could be used as heterologous molecule of interest.

A further example of heterologous molecules include growth factors, such as adenomedullin (AM), angiopoietin (Ang), autocrine motility factor, bone morphogenetic proteins (BMPs), brain-derived neutrophic factor (BDNF), epidermal growth factor (EGF), erythropoietin (EPO), fibroblast growth factor (FGF), glial cell line-derived neutrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), mystatin (GDF-8), nerve growth factor (NGF), platelet-derived growth factor (PDGF), thrombopoietin (TPO), transforming growth factor alpha (TGF-α), transforming growth factor beta (TGF-β), tumor necrosis factor alpha (TNF-α), vascular endothelial growth factor (VEGF), placental growth factor (PIGF), etc. A nanomotor with a growth factor linked to a surface-binding peptide can be used to provide a surface with, for instance, capability of stimulating cellular growth, proliferation and/or cellular differentiation.

Further examples of heterologous molecules of interest include cell growth inhibitors and chemotherapeutic agents. Such a type of heterologous molecules will, when included in the nanomotor, provide a local cell growth inhibiting effect. Non-limiting examples of such heterologous molecules of interest include farnesyl transferase inhibitors; alkylating agents, such as nitrogen mustards, e.g. mechlorethamine, cyclophosphamide, melphalan, chlorambucil, ifosfamide and busulfan; nitrosoureas, e.g. N-nitroso-N-methylurea (MNU), carmustine (BCNU), lomustine (CCNU), semustine (MeCCNU), fotemustine and streptozotocin; tetrazines, e.g. dacarbazine, mitozolomide and temozolomide and aziridines, e.g. thiotepa, mytomycin, diaziquone (AZQ); and cisplatines, e.g. cisplatine, carboplatin and oxaplatin; antimetabolites, such as anti-folates, e.g. methotrexate and pemetrexed; fluropyrimidines, e.g. fluorouracil and capecitabine; deocynucleoside analogues, such as cytarabine, gemcitabine, decitabine, Vidaza, fludarabine, nelarabine, cladribine, clofarabine and pentostatine; and thiopurines, e.g. thiguanine and mercaptopurine; anti-microtubule agents, such as vinca alkaloids, e.g. vincristine, vinblastine, vinorelbine, vindesine and vinflunine; and taxanes, e.g. paclitaxel and docetaxel; and podophyllotxin; topoisomerase inhibitors, such as irinotecan, topotecan, captothecin, etoposide, doxorubicin, mitoxantrone, teniposide, novobiocine, merbarone and aclarubicin; cytotoxic antibiotics, such as antracyclines, e.g. doxorubicin, daumorubicin, epirubicin, idarubicin, pirarubicin, aclarubicin, mitoxantrone, actinomycin, bleomycin, plicamycin, and mitomycin.

Other groups of heterologous molecules of interest include polynucleotides such as DNA or RNA molecules. The heterologous molecule can also be a nanosensor or a molecular gate. "Discontinuously attached over the whole surface" refers to a discrete distribution that is not restricted to a single face or hemisphere of the particle, that is, it refers to a nonpolar distribution. It does not mean, however, that the molecule is covering the whole surface of the particle in a homogenous manner. The particles of the invention may present the molecules externally attached forming discrete patches over the whole surface of the particle, or which is the same, presenting gaps wherein no molecules are attached.

As used herein, "targeting molecule" refers to a molecule having specificity for a particular cell, tissue, or organ. Preferred examples of targeting molecules include but are not limited to antibodies, growth factors, and polysaccharides.

As used herein, "nanosensor" refers to any nano or micro scale sensing device. The nanosensors of the invention are able to detect and respond to changes in the environment where they are located. In particular, the nanosensors of the invention can be nanoswitches, which are nanosensors able to switch between two distinct forms. DNA-nanoswitches contain a single strand DNA molecule with a conformation that changes in response to an environmental change, for instance a pH change. The DNA molecule may be coupled to fluorescent molecules that allow the detection of the conformational change.

As used herein, "labelling molecule" refers a molecule which can be chemically bound to the nanomotor and which emits a detectable signal enabling the nanomotor to be detected. Particularly preferred examples of labelling molecules include but are not limited to chemiluminescent molecules, fluorescent molecules and isotopes.

As used herein, "molecular gate" or "nanovalve" refers to a molecular system on a nano or micro scale that switches between a first closed form and a second open form in response to a selected trigger, such as light, temperature, magnetic fields and pH. The closed form is design to block the release of the cargo contained in the particle to which de molecular gate is attached. Upon application of the trigger, the gate changes to the open form allowing the release of the cargo.

An "anticancer antibody" refers to an antibody with the capacity to arrest or eliminate cancer cells.

As mentioned above, the invention provides in a first aspect an enzyme-powered nanomotor externally functionalized with a heterologous molecule.

In a particular embodiment of the first aspect, optionally in combination with any of the embodiments provided above or below, the particle is a nanoparticle or a microparticle.

The term "nanoparticle" as used herein, refers to a particle with at least two dimensions at the nanoscale, particularly with all three dimensions at the nanoscale. For analogy, the term "microparticle" as used herein, refers to a particle with at least two dimensions at the microscale, particularly with all three dimensions at the microscale In a particular embodiment, the particle is from 1 nm to 100 μm. In particular, from 30 nm to 2 μm. More in particular, from 100 nm to 1 μm. Even more in particular, from 400 nm to 600 nm.

As regards the shape of the nanoparticles or microparticles described herein, there are included spheres, polyhedral and rod-shape. Particularly, when the nanoparticle or microparticle is substantially rod-shaped with a substantially circular cross-section, such as a nanowire or a nanotube, microwire or microtube, the "nanoparticle" or "microparticle" refers to a particle with at least two dimensions at the nanoscale or microscale, these two dimensions being the cross-section of the nanoparticle or the microparticle.

In a particular embodiment of the first aspect, optionally in combination with any of the embodiments provided above or below, the particle is spherical As used herein, the term "size" refers to a characteristic physical dimension. For example, in the case of a nanoparticle/microparticle that is substantially spherical, the size of the nanoparticle/microparticle corresponds to the diameter of the nanoparticle/microparticle.

When referring to a set of nanoparticles/microparticles as being of a particular size, it is contemplated that the set can have a distribution of sizes around the specified size. Thus, as used herein, a size of a set of nanoparticles/microparticles can refer to a mode of a distribution of sizes, such as a peak size of the distribution of sizes. In addition, when not perfectly spherical, the diameter is the equivalent diameter of the spherical body including the object. This diameter is generally referred as the "hydrodynamic diameter", which measurements can be performed using a Wyatt Möbius coupled with an Atlas cell pressurization system or Malvern. Transmission Electron Microscopy (TEM) or Scanning Electron Microscopy (SEM) images do also give information regarding diameters.

A wide variety of particle materials are available to the skilled person, and he would understand that the material chosen would depend on the intended application of the nanomotor, for instance, nanomotors for therapeutic uses should be made with biocompatible particles.

Thus, in a particular embodiment of the first aspect, optionally in combination with any of the embodiments provided above or below, the particle is made of a material selected from the group consisting of metal, metal oxide, polymer, lipid, protein, cell membrane, cell body, carbonaceous material, and mixtures thereof. In a particular embodiment, the metal is aluminum (AI), platinum (Pt), palladium (Pd) or magnesium (Mg). In a particular embodiment, the metal oxide is selected from silica ($SiO_2$), manganese oxide ($MnO_2$) and titanium oxide ($TiO_2$). In a particular embodiment the polymer is polystyrene or metallic organic frameworks. In a particular embodiment, the carbonaceous material is selected from carbon, graphene, and fullerene. In a particle embodiment, the material of the particle is a polymersome. In a particle embodiment, the particle is a protein-based particle (proteinsome). In a particular embodiment, the cell body is a platelet or a red blood cell (RBC).

The term "metallic organic framework" or "MOF" refers to compounds comprising metal ions or clusters coordinated to organic ligands. The central metallic element may be at least one selected from the group consisting of zinc (Zn), cobalt (Co), cadmium (Cd), nickel (Ni), manganese (Mn), chromium (Cr), copper (Cu), lanthanum (La), iron (Fe), platinum (Pt), palladium (Pd), silver (Ag), gold (Au), rhodium (Rh), iridium (Ir), ruthenium (Ru), lead (Pb), tin (Sn), aluminum (AI), titanium (Ti), molybdenum (Mo), tungsten (W), vanadium (V), niobium (Nb), tantalum (Ta), scandium (Sc), yttrium (Y), gallium (Ga), germanium (Ge), indium (In), bismuth (Bi), selenium (Se), and antimony (Sb). The organic ligand may include a functional group that is linkable to at least two metallic ions.

"Cell membrane" refers to the lipid bilayer that forms a continuous barrier around cells. The particles of the invention can be formed of prokaryotic or eukaryotic cell membranes.

As used herein, "cell body" refers to the part of a cell that contains the genetic material surrounded by the cytoplasm and the plasma membrane.

The term "polymersome" refers to artificial vesicles made of amphiphilic synthetic block copolymers, The term "proteinosome" refers to particles composed of self-assembled proteins or protein-polymer conjugates.

In a particular embodiment, optionally in combination with any of the embodiments provided above or below, the particle is made of mesoporous silica. As used herein, "mesoporous silica" refers to porous silica having medium-sized pores regularly arranged, specifically, the pores are from 2 nm to 50 nm, and more specifically, from 4 nm to about 40 nm.

In a particular embodiment of the first aspect, optionally in combination with any of the embodiments provided above or below, the enzyme is selected from the group consisting of oxidoreductase, hydrolase and lyase. In a more particular embodiment, the enzyme is selected from the group consisting of glucose oxidase, urease, catalase, glutamate oxidase, xanthine oxidase, peroxidase, bilirubin oxidase, lipase, protease and combinations thereof. In a more particular embodiment, the enzyme is urease. The term urease (EC 3.5.1.5) refers to the group of enzymes that catalyze the hydrolysis of urea into carbon dioxide and ammonia. In a particular embodiment of the invention, the urease is from *Canavalia ensiformis* (CAS Number 9002-13-5). In a more particular embodiment, it is a Type IX urease from *Canavalia ensiformis* (CAS Number 9002-13-5). The sequence of the enzyme can be found in various databases, such as Uniprot (P07374 UREA_CANEN, Jan. 2, 1994 update) In a particular embodiment of the first aspect, optionally in combination with any of the embodiments provided above or below, the heterologous molecule is selected from the group consisting of a targeting molecule, a labelling molecule, a nanosensor and a molecular gate.

In a particular embodiment of the first aspect, optionally in combination with any of the embodiments provided above or below, the heterologous molecule is an antibody. In a more particular embodiment, the antibody is an anticancer antibody. In a more particular embodiment, the anticancer antibody binds a membrane receptor. In a more particular embodiment, the membrane receptor is a FGFR (fibroblast growth factor receptor) selected from the group consisting of FGFR1, FGFR2, FGFR3, and FGFR4. In a more particular embodiment, the FGFR is FGFR3.

In a particular embodiment of the first aspect, optionally in combination with any of the embodiments provided above or below, the heterologous molecule is a nanosensor. There are numerous nanosensors available for the skilled in the art (Campuzano S. et al., "Motion-driven sensing and biosensing using electrochemically propelled nanomotors", Analyst. 2011, vol. 36(22), pp. 4621-30). In a particular embodiment, the nanosensor is a DNA-nanoswitch. DNA-nanoswitches are molecular complexes comprising a single strand DNA molecule coupled to a fluorophore-quencher pair. In a particular embodiment, the sequence of the DNA molecule of the DNA-nanoswitch has at least 85%, 86%, 87%, 88%, 89%, 90%, 91%, 92%, 93%, 94%, 95%, 96%, 97%, 98%, 99% or 100% sequence identity with SEQ ID NO: 1.

In a particular embodiment, the nanosensor is a nanoparticle. In a more particular embodiment, the nanosensor is a metal nanoparticle. More particularly, the metal nanoparticle is a gold (Au) nanoparticle. The skilled in the art would understand that the nanoparticle forming the nanosensor has to be smaller than the nanoparticle or microparticle forming the nanomotor.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

In a particular embodiment of the first aspect, optionally in combination with any of the embodiments provided above or below, the nanomotor further comprises a cargo. In a particular embodiment, the cargo is selected from the list consisting of a drug, wherein the drug is selected from the group consisting of a small molecule, a nucleic acid, a therapeutic enzyme, a peptide, a protein or a hormone. For "cargo" it is understood any molecule transported within the nanomotor to be delivered at the desired target. Depending on the surface material and porosity of the particle, the cargo can be inside the particle or adsorbed to its surface.

In a particular embodiment, the drug is a cytotoxic drug. More particularly, it is an anticancer drug.

In a particular embodiment of the first aspect, optionally in combination with any of the embodiments provided above or below, the enzyme and the heterologous molecule are attached to the surface of the particle directly or through a linker. In a more particular embodiment, the linker is selected from the group consisting of anhydrides, alcohols, acids, amines, epoxies, isocyanates, silanes, halogenated groups, and polymerizable groups, preferably 3-aminopropyltriethoxysilane (APTES). In an even more particular embodiment, the linker is glutaraldehyde.

In such an aspect, one part of the linker is bound to the surface of the particle, and another part of the linker is bound to the enzyme or heterologous molecule, thereby forming a covalent bond between the enzyme or heterologous molecule and the surface. The bond between the linker and said surface and said enzyme or heterologous molecule is effected by chemical reactions occurring between the linker and the enzyme or heterologous molecule thereby securing a covalent bond between the surface and said enzyme or heterologous molecule. In one embodiment, the enzyme and/or the heterologous molecule are attached to the surface of the particle after a chemical pre-treatment of said surface of the particle.

As mentioned above, in a second aspect the invention provides a pharmaceutical composition comprising a therapeutically effective amount of the nanomotor of the first aspect and a pharmaceutically acceptable excipient and/or carrier.

The expression "therapeutically effective amount" as used herein, refers to the amount of the nanomotor that, when administered, is sufficient to prevent development of, or alleviate to some extent, one or more of the symptoms of the disease or disorder which is addressed. The particular dose of agent administered according to this invention will of course be determined by the particular circumstances surrounding the case, including the nanomotor administered, the route of administration, the particular condition being treated, and the similar considerations.

The expression "pharmaceutical composition" encompasses both compositions intended for human as well as for non-human animals (i.e. veterinarian compositions).

The expression "pharmaceutically acceptable carriers or excipients" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the nanomotor, the pharmaceutically acceptable excipients, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavoring agents can be present in the composition, according to the judgment of the formulator.

The pharmaceutical compositions containing the nanomotor of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding excipients include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

As mentioned before, the invention also provides in a third aspect the nanomotor or the pharmaceutical composition of the invention for use in therapy, diagnosis or prognosis. Urease-propelled nanomotors are capable of moving not only in liquid media, such as urine, but also in viscous media such as hyaluronic acid. Moreover, they are also active in mucous secretions. Therefore, the nanomotors of the invention can be used both in liquid and viscous tissues, such as in the aqueous humour of the eye.

In a particular embodiment of the third aspect, optionally in combination with any of the embodiments provided above or below, the nanomotor of the first aspect or the pharmaceutical composition of the second aspect is for use in the treatment of cancer.

This embodiment can also be formulated as the use of the nanomotor of the first aspect, or the pharmaceutical composition of the second aspect for the manufacture of a medicament for the treatment and/or prevention of cancer. This aspect can also be formulated as a method for treating and/or preventing cancer, the method comprising administering a therapeutically effective amount of the nanomotor of the first aspect or the pharmaceutical composition of the second aspect, to a subject in need thereof.

Illustrative non-limiting examples of cancer which can be treated with the nanomotor or the pharmaceutical composition of the invention include, although they are not limited to, papillomas, adenomas, lipomas, osteomas, myomas, angiomas, nevi, mature teratomas, carcinomas, sarcomas. immature teratomas, melanoma, myeloma, leukaemia, Hodgkin's lymphoma, basalioma, spinalioma, breast cancer, ovarian cancer, uterine cancer, bladder cancer, lung cancer, bronchial cancer, prostate cancer, colon cancer, pancreatic cancer, kidney cancer, esophageal cancer, hepatocarcinoma, head and neck cancer, etc. In a particular embodiment of the third aspect, the cancer is bladder cancer.

From the data herein provided, the skilled in the art would understand that the nanomotors and pharmaceutical compositions of the invention may also be useful in the treatment of other diseases such as metabolic, neurologic and inflammatory diseases.

As mentioned above, in a fifth aspect the invention provides an in vitro method of detecting an analyte in an isolated sample, which comprises contacting the nanomotor as defined in the first aspect with the sample. The skilled in the art would understand that the nanomotors of the invention can be adapted to detect different analytes through their functionalization with sensors of said analytes.

In a particular embodiment of the fifth aspect, optionally in combination with any of the embodiments provided above or below, the sample is a biological isolated sample. More particularly, the biological isolated sample is blood, plasma or serum.

As mentioned above, in a sixth aspect the invention provides the use of the nanomotor as defined in the first aspect in an in vitro method for detecting an analyte in an isolated sample.

In a particular embodiment of the fifth or sixth aspects, optionally in combination with any of the embodiments provided above or below, the sample is a liquid sample. As mentioned before, the nanomotors of the inventors are capable of moving in liquids with various degrees of viscosity. For instance, they can move in urine, which has a kinematic viscosity of: 1.0700 cSt at 20° C. (measured by Inman et al., "The impact of temperature and urinary constituents on urine viscosity and its relevance to bladder hyperthermia treatment", Int J Hyperthermia, 2013, vol. 29(3), pp. 206-10), and Hyaluronic acid at the concentration found in the synovial fluids (1 mg/ml, around 10-2 Pa*s for a range of 1 to 10 Hz of shear rate, measured in a rheometer).

The nanomotors of the invention are particularly useful for the detection of a wide variety of analytes, such as pollutants or biomarkers, Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

1. Targeting 3D Bladder Cancer Spheroids with Urease-Powered Nanomotors
1.1. Methods
Materials Ethanol (EtOH, 99%), methanol (MeOH, 99%), hydrochloric acid (37% in water), ammonium hydroxide (25% in water), tetraethylorthosilicate (TEOS, 99%), triethanolamine (TEOA, 99%), cetyltrimethylammonium bromide (CTAB, 99%), 3-aminopropyltriethoxysilane (APTES, 99%), glutaraldehyde (GA, 25% in water), urease (from *Canavalia ensiformis*, Type IX, powder, 50 000-100 000 units/g solid), Urease Activity Assay Kit (Sigma-Aldrich), urea (99.9%), glycerol (99%), sodium borohydride powder (NaBH$_4$, 98.0%), formaldehyde solution (37% in water), bovine serum albumin (lyophilized powder), 4-nitrophenol solution (10 mM), sodium chloride puriss. (NaCl), potassium chloride anhydrous (KCl), sodium phosphate monobasic (NaH$_2$PO$_4$), sodium bicarbonate BioXtra (99.5-100.5%, NaHCO$_3$), dimethyl sulfoxide (DMSO, 99.9%), and HS-PEG5K-NH$_2$ (HCl salt) were purchased from Sigma-Aldrich. Pierce™. BCA Protein Assay Kit, Wheat Germ Agglutinin (WGA AlexaFluor™ 647 conjugate), Goat anti-Mouse IgG (H+L) Alexa Fluor™ 488 conjugate, 3-(4,5-dimethylthiazol-2-yl)-2,5-diphenyltetrazolium bromide (MTT), and phosphate buffer saline (PBS) were purchased from Thermo Fisher Scientific. Matrigel™ basement matrix was purchased from Corning. Anti-FGFR3 antibody (ab89660) was purchased from Abcam. Hoechst 33342 was purchased from Life Sciences. Spectra/Por® 7 Standard RC pre-treated Dialysis Tubing (3.5 kD) was purchased from Spectrum. Cyanine3 NHS ester was purchased from Lumiprobe. McCoy's 5A (modified) medium, Penicillin Streptomycin solution, Fetal Bovine Serum (FBS) and Trypsin 0.5% EDTA were purchased from Gibco. LIVE/DEAD™ Viability/Cytotoxicity Kit was purchased from Invitrogen. Human urinary bladder transitional cell papilloma RT4 cells were obtained from ATCC (Rockville, MA).

Instruments

Transmission Electron Microscopy (TEM) images were captured using a JEOL JEM-2100 microscope. Scanning Electron Microscopy (SEM) images were captured using a FEI NOVA NanoSEM 230 at 10 kV. Hydrodynamic radii and electrophoretic mobility measurements were performed using a Wyatt Möbius coupled with an Atlas cell pressurization system. The Brunauer-Emmett-Teller (BET) analysis was carried out using a Micromeritics Tristar II Plus automated analyzer. Optical videos as well as cell culture imaging were performed using an inverted optical microscope (Leica DMi8) equipped with a 63× water objective, a galvo stage and filter cubes for FITC, Rhodamine, DAPI and CY5. Protein quantification and enzymatic activity assays were carried out using an Infinite M200 PRO Multimode Microplate Reader. The confocal microscopy analysis was performed using a LSM 800-Zeiss equipped with a 63× oil objective.

Synthesis of Mesoporous Silica Nanoparticles (MSNPs): The MSNPs were prepared using a sol-gel method. Briefly, a solution containing CTAB (570 mg), TEOA (35 g), and water (20 mL) was heated to 95° C. in a silicon oil bath. This mixture was stirred for 30 minutes, and subsequently TEOS (1.5 mL) was added dropwise. The mixture was further stirred at 95° C., for 2 hours. The produced particles were collected by centrifugation and washed with ethanol (3 times, 1350 g, 10 minutes). Then, the particles were suspended in a MeOH:HCl mixture (30 mL, 10:0.6) and refluxed at 80° C. for 24 hours, for removal of CTAB from the MSNPs' pores. Finally, the particles are collected by centrifugation and washed in ethanol (3 times, 1350 g, 10 minutes), sonicating 20 minutes between each centrifugation. Aliquots (0.5 mL) were collected, centrifuged and air-dried to determine the concentration of the MSNPs suspension.

Amine Functionalization of MSNPs (MSNP-NH$_2$): The previously synthesized MSNPs were suspended in EtOH (2 mg/mL). Then, APTES was added to the suspension (10 µL/mg of MSNP) and it was shaken for 24 hours at room temperature, using an end-to-end rotary shaker. Finally, the particles were collected by centrifugation and washed in ethanol (3 times, 1350 g 10 minutes) and in water (3 times, 1928 g 10 minutes), sonicating 20 minutes between each centrifugation. Aliquots (0.5 mL) were collected, centrifuged and air-dried to determine the concentration of the MSNPs suspension. Functionalization of MSNP-NH$_2$ with Urease and Heterobifunctional H$_2$N-PEG-SH (MSNP-Ur/PEG): MSNP-NH$_2$ were centrifuged at 1340 g for 10 minutes, suspended in 900 µL of PBS (2 mg/mL) and sonicated for 20 minutes. After this, 100 µL of glutaraldehyde were added and the mixture was vortexed for 30 seconds to obtain a good dispersion. The mixture was placed on an end-to-end rotary shaker for 2.5 hours, at room temperature. The nanoparticles were then collected and washed three times with PBS (1340 g, 10 minutes) and sonicated for 20 minutes between each wash. Next, the GA-activated nanoparticles were suspended in solution of PBS containing urease (3 mg/mL) and H$_2$N-PEG-SH (1 µg/mg of MSNP-NH$_2$). The mixture was then placed on an end-to-end rotary shaker overnight, at room temperature. The resulting nanomotors were washed three times with PBS by centrifugation (1340 g, 10 minutes), intercalating the washes with 3 minutes of sonication.

Functionalization of PEGylated Urease Nanomotors with anti-FGFR3 antibody (MSNP-Ur/PEG-Ab): The nanomotors were suspended in PBS (2 mg/mL) and anti-FGFR3 antibody (30 µg of antibody per mg of nanomotors) was added. The mixture was then incubated overnight in the rotary shaker, at room temperature. Finally, the antibody-modified nanomotors were collected by centrifugation (1340 g, 10 minutes) and washed three times with PBS, intercalating the washes with 3 minutes of sonication. Hydrodynamic Radii and Surface Charge Analysis: A Wyatt Möbius DLS, coupled to an ATLAS pressurizer was used to characterize the size distribution and surface charge of MSNP, MSNP-NH$_2$, MSNP-Ur/PEG and MSNP-Ur/PEG-Ab. The equipment uses a 532 nm wavelength laser and a detector angle of 163.5°. The samples analyzed were diluted to a concentration 0.3 mg/mL and analyzed for light scattering and electrophoretic mobility simultaneously, with an acquisition time of 5 seconds, performing 3 runs per measurement. A total of 9 measurements were performed to obtain statistical relevant data.

Quantification of Urease and Antibody Amounts on MSNP: The concentration of urease present on MSNP-Ur/PEG was measured using the BCA Protein Assay Kit from Thermo Fisher Scientific, according to manufacturer's instructions. This kit correlates the quantity of proteins with the reduction of copper by peptide bonds. The same procedure was repeated for MSNP-Ur/PEG-Ab, in order to quantify the amount of antibody bound to the nanomotors.

Urease Activity Assay: enzymatic activity of urease while bound to MSNPs was evaluated using a commercial kit that determines the concentration of ammonia generated by Berthelot's method (Patton, C. J. et al., "Spectrophotometric and Kinetics Investigation of the Berthelot Reaction for the Determination of Ammonia", Anal. Chem., 1977, vol. 49, pp. 464-469). The nanomotors were at a concentration of 0.5 mg/mL and the experiment was performed according to manufacturer's instructions.

Urease Labeling with Cy3: Urease (22 mg) was dissolved in 1 mL of sodium bicarbonate buffer (100 mM). Next, 7 µL of a Cy 3 solution in DMSO (5 mM) were added to the urease solution, and the mixture was incubated for 4 hours, at room temperature and shaking in the dark. The solution of labelled urease was then dialyzed (3.5 kD pore membrane) for 24 hours to eliminate non-reacted Cy3 molecules.

Quantification of Ammonia Production by MSNP-Ur/PEG: The ammonia produced by nanomotors was quantified using a titration method. For this, the nanomotors were incubated with different urea concentrations (12.5, 25, 50, 100, 200, and 300 mM) and the samples were analyzed at different time points (5, 15, 60, 120, 240 minutes and at 24 hours). At each time point, the suspensions of nanomotors was centrifuged and the supernatant was titrated with HCl (10 mM), using p-nitrophenol as indicator.

Optical Video Recording of Nanomotors and MSD Analysis: An inverted microscope equipped with a 63× water objective was used to observe and record videos of the nanomotors movement. Samples of aqueous solutions of simulated urine containing nanomotors were placed in a glass slide and mixed well with simulated urine at a range of urea concentrations (12.5, 25, 50, 100, 200, and 300 mM). The samples were then covered with a glass slide to avoid artifacts caused by drifting and videos of 30 seconds were recorded. The videos were acquired using a Hamamatsu camera, at a frame rate of 50 fps, in bright field. At least 20 nanomotors are analyzed per condition. The videos were analyzed using a python-based code to obtain the trajectories of the nanomotors, and compute the mean-squared displacement (MSD) following:

$$\text{MSD}(\Delta t) = \langle (x\_i(t+\Delta t) - x\_i(t))^2 \rangle, \ i=2, \text{ for 2D analysis}$$

After this, the diffusion coefficient ($D_e$) was obtained by fitting the MSD data to equation 2, which is valid at short time intervals for small particles, with low rotational diffusion. 3D Cell Culture: Human urinary bladder transitional cell papilloma RT4 cells were cultured in McCoy's 5A (Modified) Medium, supplemented with FBS (10%) and penicillin-streptomycin solution (1%), in a 37° C. and 5% CO2 atmosphere. The cells were split every 4 days at a 1:2 ratio. To obtain 3D RT4 cell cultures, 8-well ibidi dishes were pre-coated with 23 μL of Matrigel™ (5 mg/mL) and incubated at 37° C. for 30 minutes, allowing the gel to form. Next, 30 μL of a suspension of RT4 cells at a density of 5×10⁶ cells/mL was spread evenly in each well and the dishes were incubated for 30 minutes at 37° C. Finally, 150 μL of RT4 McCoy's medium containing 10% of Matrigel™ was added. The cultures were allowed to grow for 7 days before the experiments, changing the medium every 2 days.

Immunostaining of FGFR3 Transmembrane Protein in 3D RT4 Cell Cultures: the 3D cultures described above were washed 3 times with PBS 1×. Then, the surface of the wells was gently scratched with a pipette tip and the culture was suspended in McCoy's medium in a tube. The tubes were briefly spinned and the supernatant was removed. Next, the cells were suspended in formaldehyde (3.7%), placed in an 8-well dish and incubated for 15 minutes at room temperature. Following, the culture was washed with PBS 1×, a solution of PBS-BSA (5%) was added and the dish was incubated for 40 minutes at room temperature. Then, the anti-FGFR3 was added to the culture at a proportion of 1:50, and the dish was incubated for 24 hours, at 37° C., in a 5% CO₂ atmosphere. After, the culture was washed 3 times with PBS 1×, the secondary antibody (labeled with AlexaFluor 488) was added in a proportion of 1:500 and the dish was incubated for 40 minutes, at room temperature in the dark. Finally, the culture was washed 3 times with PBS 1×, the nuclei were labeled with Hoescht and a solution of glycerol in PBS (70%) was added. The culture was observed using confocal microscopy.

Cytotoxicity Assays: The viability of RT4 3D cultures was quantified using the Alamar Blue assay and visualized using the LIVE/DEAD viability kit following manufacturer's instructions. For this, RT4 cells were culture as mentioned above and at day 7 were incubated with each treatment—Ammonia (1 mM, 1.5 mM, 3 mM, 5 mM, 10 mM and 20 mM, for 24 hours), Urea (25 mM, 30 mM, 40 mM and 50 mM, for 24 hours), MSNP-Ur/PEG (12.5 μg/mL, at a range of urea concentrations—25 mM, 30 mM, 40 mM and 50 mM, for 1, 2 and 4 hours). After, the cultures were washed with medium, kept resting for 24 hours and viability was investigated according to manufacturer's instructions.

Furthermore, viability was also assessed at 48 h time point.

Imaging of RT4 3D Cultures and Nanomotors: At day 7, the 3D cell cultures were incubated with each treatment (MSNP-Ur/PEG or MSNP-Ur/PEG-Ab, 12.5 μg/mL) for 4 hours. At each time point, the cultures were washed and kept in a 37° C. and 5% CO2 atmosphere for 24 hours. Then, the cultures were labeled WGA 647 (membranes) and imaged using an inverted fluorescence microscope equipped with a 63× objective and a galvo stage, as well as filter cubes for Rhodamine, FITC, DAPI and Cy5.

1.2. Results and Discussion

Fully mesoporous silica nanoparticles (MSNPs) were prepared using sol-gel chemistry, where cetyltrimethylammonium bromide (CTAB) was used as porogenic agent and triethanolamine (TEOA) was used as base catalyst. The prepared MSNPs were characterized by scanning electron microscopy (SEM). SEM analysis revealed good monodispersity of the sample (polydispersity index=0.114) and a mean diameter of 481+2 nm (N=150, average size±standard error of the mean (SE)). Furthermore, the porous structure of the MSNPs was evaluated by transmission electron microscopy. A clear radial porosity was evidenced by the TEM. This crystalline configuration was further confirmed by the Fast Fourier Transform, which indicated the periodicity of the porous pattern. The surface area of the nanoparticles was studied by performing nitrogen adsorption/desorption, using Brunauer-Emmett-Teller analysis (BET) method. The MSNPs showed a type IV isotherm, typical of mesoporous silica structures, and a BET specific surface area of 1184.8 m²/g, with an average pore size of 2 nm.

The produced particles were then functionalized with amine groups by using amynopropyltriethoxysilane (APTES). The amine groups on the surface of the MSNP are later activated with glutaraldehyde (GA), that acts as a linker between the particle and the urease and heterobifunctional polyethylene glycol (PEG) molecules (FIG. 1A). The terminal thiol group of PEG allows for the coupling of the targeting moiety, anti-fibroblast growth factor 3 (anti-FGFR3).

The functionalization steps were followed by dynamic light scattering (DLS) and electrophoretic mobility analysis to obtain the hydrodynamic radii and surface charge, respectively. The DLS analysis of the as-synthesized MSNPs showed a broad peak suggesting the presence of aggregates in the suspension. Electrophoretic mobility analysis of MSNPs indicated a surface charge of −26.81±0.35 mV (N=9, average±SE), typical for silica nanoparticles. The successful functionalization with amines was evidenced by the pronounced change in surface charge to a strongly positive value (33.6±1.0 mM, N=9, average±SE), characteristic of the presence of free amine groups on the surface. The hydrodynamic radii of amine functionalized MSNPs (MSNP-NH$_2$) indicated a sharper peak that can be due to a stabilization of the particles by both surface charge and surface chemistry.

The subsequent functionalization step concerned the coupling of both urease enzyme and heterobifunctional PEG. Typically, PEG is used as a spacer or as a means of preventing aggregation in suspension by providing steric hindrance between particles. We confirmed this effect on the colloidal stability of MSNP-Ur/PEG by DLS analysis, where a sharp single population peak was observed. Furthermore, the PEG molecules allowed for the conjugation of the antibodies to the nanoparticles, by linking the free thiol group at the outer end of the PEG to the antibodies' cysteine residues. This approach provides more specificity on the binding of IgG antibodies, due to the high content of cysteine residues present on the constant region of the heavy chain (FIG. 1A). The conjugation of MSNP-Ur/PEG with anti-FGFR3 antibody (MSNP-Ur/PEG-Ab) was also analyzed by DLS, and the observed single peak showed that the presence of the antibody did not affect the stability of the particles in solution. We have confirmed the presence of urease, as well as the antibody on the surface of the MSNPs, using a kit that quantifies proteins based on the reduction of copper by proteins' peptide bonds and evaluated the urease enzymatic activity while bound to the nanomotors.

The urease present on the surface of the MSNP-Ur/PEG and MSNP-Ur/PEG-Ab allows for the biocatalytic conversion of urea into ammonia and carbon dioxide, following the equation:

$$(NH_2)_2CO + H_2O \rightarrow CO_2 + 2NH_3$$

Figure 2:
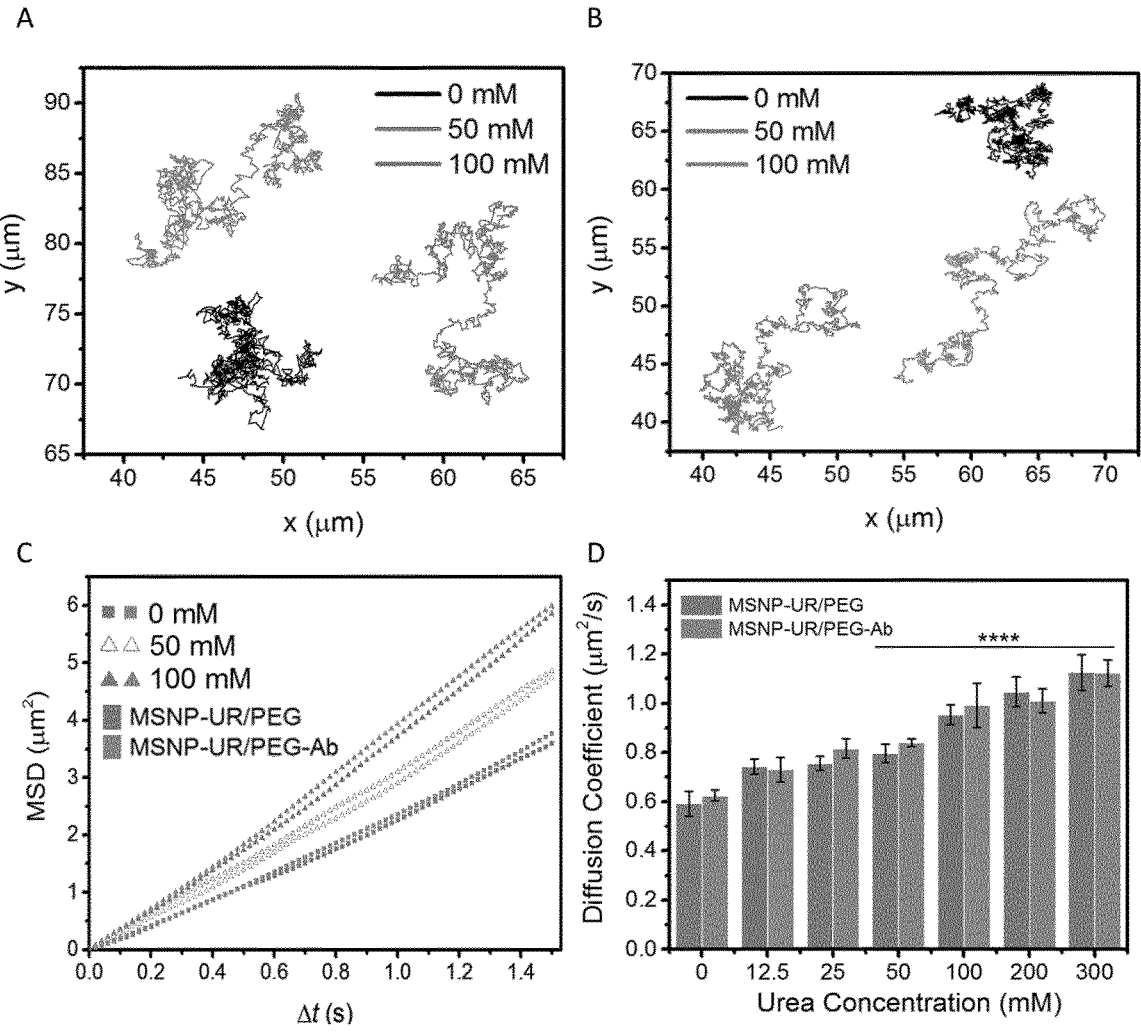
FIG. 2, related to Example 1, shows motion analysis of MSNP-Ur/PEG and MSNP-Ur/PEG-Ab. Representative tracked trajectories of A) MSNP-Ur/PEG nanomotors and B) MSNP-Ur/PEG-Ab nanomotors at 0 mM, 50 mM and 100 mM urea and C) Representative mean-squared displacements (MSD) of both types of nanomotors at 0 mM, 50 mM and 100 mM. D) Effective diffusion coefficients obtained by MSD analysis at different urea concentrations (N=20, error bars represent SE, $p < 0.001$).

Typically, a geometrical asymmetry is induced on the micro-/nanostructures (e.g. Janus particles) in order to achieve an asymmetrical generation of forces, which is an important requirement to produce motion at low Reynolds number. However, recently, it has been reported that for the motors propelled via biocatalytic conversion, a molecular unbalanced distribution of enzymes is sufficient for the generation of the asymmetry necessary to generate net motion. Yet, that previous study was reported for micron-sized motors. The MSNP-Ur/PEG and MSNP-Ur/PEG-Ab nanomotors reported in this work rely on such inherent asymmetries for self-propulsion in nano-scaled motors. The motion profiles of MSNP-Ur/PEG and MSNP-Ur/PEG-Ab were evaluated in the presence of a range of urea concentrations (0 mM, 12.5 mM, 25 mM, 50 mM, 100 mM, 200 mM and 300 mM), in simulated urine. It was used optical tracking technique to obtain the tracked trajectories of the nanomotors (FIGS. 2A&B), which were then used to calculate the mean-squared displacement (MSD). FIG. 2C displays the typical MSD of urease/PEG nanomotors and antibody-modified nanomotors in simulated urine. We observed that the MSD increases linearly with time, which is characteristic of diffusive motion, and obtained the effective diffusion coefficient for each given condition by fitting the MSDs to the following equation:

$$MSD \ (\Delta t) = 4 \ D_e \ \Delta t,$$

where D$_e$ represents the effective diffusion coefficient and $\Delta t$ represents the time interval.

FIG. 2D shows the calculated effective diffusion coefficients for both MSNP-Ur/PEG and MSNP-Ur/PEG-Ab, evidencing that a significant increase in diffusion was achieved at 50 mM urea concentration (p<0.001). The diffusion coefficient further increased with increasing urea concentrations in simulated urine, reaching a plateau. The increase in diffusion with respect to increasing urea concentrations can be related with urease enzyme Michaelis-Menten kinetics, which obeys the following equation:

$$v = \frac{V_{max}[S]}{K_m + [S]}$$

where V$_{max}$ represents the maximum reaction rate, S represents substrate concentration and K$_m$ represents the Michaelis-Menten constant. As displayed in FIG. 2D, no significant differences were found between the motion profiles of MSNP-Ur/PEG and MSNP-Ur/PEG-Ab, indicating that the presence of this targeting moiety does not hinder the motion abilities of the nanomotors.

We studied the in vitro biocompatibility of the substrate required for nanomotors' motion (urea) and the by-product of the bio-catalysis (ammonia) by using 3D cultures (spheroids) of human urinary bladder transitional cell papilloma RT4 cells. The spheroids were obtained by seeding RT4 cells in dishes coated with Matrigel™ which resembles the extracellular matrix and provides a 3D environment for cell growth. Then, the cultures were allowed to proliferate for 7 days and spheroid growth was monitored every day. It was then investigated the effect of a range of concentrations of urea (0 mM, 25 mM, 50 mM and 100 mM) and ammonia (0 mM, 20 mM, 30 mM, 40 mM and 50 mM), by incubating the spheroids for 24 hours at each condition. After that, the cultures were washed with medium and cell viability and proliferation was assessed using the Alamar Blue assay. This assay is based on the reduction of resazurin into the fluorescent compound resorufin by metabolically active cells.

Urea exhibited good biocompatibility, not affecting spheroid viability even at the highest concentration we studied while ammonia revealed an increased cytotoxic trend with increasing concentrations. Nevertheless the spheroids remained viable (>70% viability) at all ammonia concentrations tested.

Figures 3, 4:
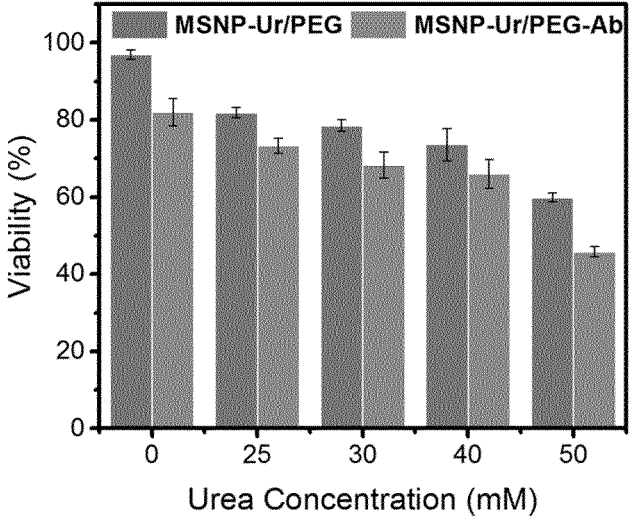
FIG. 3, related to Example 1, shows the effect of nanomotors with and without antibody on spheroids' viability in the presence of different concentrations of urea. Quantification of spheroids' viability after 4-hour incubation with MSNP-Ur/PEG (originally in blue) and MSNP-Ur/PEG-Ab (originally in red), at different urea concentrations (N=3, error bars represent SE).
FIG. 4, related to Example 1, shows the targeting and penetration abilities of antibody-modified nanomotors into bladder cancer spheroids. Quantification of the internalization of antibody-modified nanomotors into bladder cancer spheroids in the presence (40 mM) and absence of urea after 4-hour incubation, and quantification of the proliferation of spheroids incubated with MSNP-Ur/PEG and MSNP-Ur/PEG-Ab for 4 hours, in the presence (40 mM) and absence of urea at after measured after a 48-hour resting period.

It was further investigated the viability of the spheroids when exposed to the nanomotors (MSNP-Ur/PEG), under a range of concentrations of urea and at different incubation periods. The spheroids were incubated with 12.5 µg/mL of bare nanomotors or antibody-modified nanomotors at 0 mM, 25 mM, 30 mM and 40 mM of urea, for 1, 2 and 4 hours. Next, the cultures were thoroughly washed with medium to remove nanomotors and uncatalyzed urea and kept for 24 hours before analysis. The effect of the nanomotors on bladder cancer spheroids' viability was visualized using the LIVE/DEAD® viability kit and quantified using the Alamar Blue assay (FIG. 3). It was observed that the nanomotors were not toxic in the absence of urea, which indicates the good biocompatibility of the nanomotors' chassis (mesoporous silica, type MCM-41), as well as the PEG and enzyme. Upon the presence of increasing concentrations of urea, a cytotoxic effect is denoted for both nanomotors, being more pronounced on antibody-modified nanomotors (FIG. 3). The toxicity observed for bare nanomotors is due to the production of ammonia originated from the biocatalytic conversion of urea. However, the higher cytotoxic effect verified for nanomotors carrying the antibody can arise from the interaction between the anti-FGFR3 and the antigen present on the spheroids' membranes. The interaction between these moieties has been reported to block the FGF signaling pathway, which is involved on cell growth and proliferation.

To better understand the contribution of ammonia to the cytotoxic effect observed on the spheroids, it was studied the effective concentration of ammonia produced by the nano-motors for defined periods at different concentrations of urea. 12.5 μg/mL of nanomotors were incubated with a range of concentrations of urea (0 mM, 12.5 mM, 25 mM, 50 mM, 100 mM, 200 mM and 300 mM) and used p-nitrophenol as an indicator for pH. Since the conversion of urea into ammonia and carbon dioxide by nanomotors generates a sharp rise in pH, the solution containing nanomotors turns yellow due to the presence of p-nitrophenol and can be titrated with HCl to quantify the amount of ammonia present, according to the following equation:

$$NH_3 + HCl \rightarrow NH_4Cl$$

It was found that at this concentration of nanomotors, the maximum ammonia output reached was 17 mM, which was found to be biocompatible towards bladder cancer spheroids (>70% viability for 20 mM ammonia). Nevertheless, upon incubation with nanomotors and urea, the cytotoxic effect observed is stronger than with free ammonia. This outcome may emerge from the production of a locally higher concentration of ammonia by the nanomotors in the vicinity of the spheroids, thus leading to higher cytotoxicity.

Taking in consideration the nanomotors' enhanced diffusion capabilities and biocompatibility, it was subsequently investigated their potential to target and penetrate into bladder cancer spheroids (FIG. 4). Firstly, it was verified the expression of the targeted antigen (FGFR3) on the surface of the bladder cancer spheroids by immunocytochemistry, a technique used to visually detect the location of specific proteins on a sample by means of fluorescently labeled antibodies. An immunocytochemistry of a bladder cancer spheroid showed green fluorescence on the cell membranes confirming the presence of the transmembrane protein FGFR3, and blue represents the cell nuclei labeled with Hoechst.

It was then investigated the ability of nanomotors to penetrate the bladder cancer spheroids, and the effect of the presence of the targeting moiety on internalization efficiency. Furthermore, it was evaluated the influence of active motion in internalization efficiency, by incubating the spheroids with bare nanomotors or antibody-modified nanomotors in the presence of 40 mM urea. For this, urease was labeled with the fluorescent marker Cyanine3 (Cy3) prior to its functionalization onto the MSNP-NH$_2$, to precisely localize the nanomotors using fluorescence microscopy. Then, the nanomotors were functionalized with both pure urease and labeled urease (5%) and verified that the motion capabilities were retained despite of the presence of labeled enzyme. Next, the 3D cultures were incubated with 12.5 μg/mL of MSNP-Ur/PEG-Ab, or MSNP-Ur/PEG as negative control for targeting, for 4 hours, in the absence and presence of urea (40 mM). Afterwards, the cultures were washed, cell membranes were labeled with wheat germ agglutinin (WGA). Quantification of fluorescence intensity of Cy3 within spheroids (50-100 μm in diameter) revealed that active motors present a three-fold higher internalization efficiency than in the absence of urea, which can be due to the propulsive force generated by active motion. Furthermore, in the presence of urea, antibody-modified nanomotors present four times higher internalization efficiency than nanomotors without antibody (FIG. 4). This might be because when a nanomotor is actively moving, the probability of the antibody interacting with the target antigen is higher than when only Brownian diffusion is taking place. In our case, a nanomotor propelling at 40 mM urea covers 53% more area in one second than a nanomotor merely experiencing Brownian diffusion, as evidenced by the MSDs, which improves the chances of the antibody to contact with the antigen and penetrate into the spheroid.

Considering that the antibody used blocks the cells' FGF signaling pathway when bound to the antigen, it was further investigated the potential therapeutic effect of antibody-modified nanomotors by analyzing cell proliferation (inset FIG. 4). For this, the bladder cancer spheroids were incubated with MSNP-Ur/PEG-Ab for 4 hours, with and without urea, using nanomotors without antibody as a control. After, the spheroids were washed to remove uncatalyzed urea and non-internalized nanomotors, and proliferation was measured after a 48-hour resting period using the Alamar Blue assay. It was observed that spheroids incubated with bare nanomotors (without antibody) maintained the viability levels observed at 24 hours, whereas spheroids incubated with antibody-modified nanomotors decreased the viability, indicating that cell proliferation was arrested. These results point towards the applicability of nanomotors carrying the anti-FGFR3 antibody as tools for targeted bladder cancer therapy.

1.3. Conclusions

Urease-powered nanomotors comprising PEG, where the PEG acts both as a steric impediment to prevent aggregation and a linker to connect a specific bladder cancer antibody on the nanomotors' surface (anti-FGFR3) have been developed. The nanomotors, with and without antibody, present enhanced diffusion in simulated urine at a range of concentrations of urea found in bladder, which can enable their use in biomedical applications in this organ. I has been demonstrated the substrate-dependent induced toxicity of these enzymatic nanomotors using spheroids derived from human bladder cancer cells (3D cultures), which are considered to better mimic tumor environments when compared to conventional 2D cultures. Internalization phenomena was monitored at a time period similar to bladder voiding intervals and observed that active motion enhances nanomotors penetration by 3-fold. Furthermore, active antibody-modified nanomotors exhibited 4-fold higher internalization efficiency than active nanomotors without the antibody, reflecting the influence of self-propulsion and targeting on the ability of active particles to penetrate spheroids. Cell proliferation studies on spheroids indicated that, targeted nanomotors induce higher loss of viability than bare nanomotors (without antibody), indicating the therapeutic effect of the anti-FGFR3 that could arise from both suppression of cell proliferation and higher nanomotor internalization rates. These results point towards the potentials of such antibody-modified nanomotors as tools in targeted bladder cancer therapy, since the targeting capabilities of the particles are enhanced with active motion, resulting in the improvement of the therapeutic effect of the anti-FGFR3 antibody.

2. Enzyme-Powered Micromotors Modified with DNA Nanoswitches for Local pH Monitoring

2.1. Materials and Methods

Chemicals

Unmodified and fluorophore-tagged DNA oligonucleotides were synthesized and purified (HPLC purification) by IBA GmBH (Gottingen, Germany) and used without further purification. The sequences of the DNA constructs are reported below.

DNA Sequences
pH-responsive DNA nanoswitch
5'-*TCCTTGTCTGTCTGTCTGTC* TTTTTT GAAGAAGGAA

TTT(Cy3)A TTCCTTCTTC <u>GTTTG</u> CTTCTTCCTT (Cy5)-3'

Amino-modified DNA-Scaffold
5'-GACAGACAGACAGACAAGGA-NH₂-3'

Control Switch
5'-*TCC TTG TCT GTC TGT CTG TC* <u>T</u> (Cy3) GAACG TTTTT

CGTTC (Cy5)

| Name | SEQ ID | Sequence |
|---|---|---|
| nanoswitch | SEQ ID NO: 1 | TCCTTGTCTGTCTGTCTGTCT TTTTTGAAGAAGGAATTTATT CCTTCTTCGTTTGCTTCTTCC TT |
| scaffold | SEQ ID NO: 2 | GACAGACAGACAGACAAGGA-NH₂ |
| Control switch | SEQ ID NO: 3 | TCCTTGTCTGTCTGTCTGTCT GAACGTTTTTCGTTC |

For all the sequences above the bases in bold represent the loop for the duplex portion and the underlined bases represent the loop for the parallel triplex region. Both the pH-responsive DNA nanoswitch and the control switch have a portion (here in italics) that is fully complementary (20-bases) to the amino-modified DNA-scaffold.

Buffer Conditions

All DNA oligomers were stored (100 μM) in 1×PBS.

Fluorescence Measurements

Fluorescence measurements were carried out on a Cary Eclipse Fluorimeter (Varian), setting excitation wavelength to $\lambda_{ex}$=530 nm (slit$_{ex}$=5 nm) and acquisition between 540 and 700 nm (slit$_{em}$=5 nm) using quartz cuvettes of reduced volume (100 μL). All measurements were performed at T=25° C. in 10 mM HEPES. Switches were first diluted in HEPES 10 mM at the concentration of 1 μM. This stock solution was then diluted to 20 nM in the same buffer whose pH was adjusted to the desired value (pH between 5.0 to 9.0).

Fluorescence Data Analysis

The ratiometric FRET has been calculated as following:

$$Rat.FRET = \frac{F_{Cy5}}{F_{Cy3} + F_{Cy5}}$$

Where $F_{Cy5}$ is the maximum fluorescence emission of Cy5 ($\lambda_{em}$=670 nm) and $F_{Cy3}$ is the maximum fluorescence emission of Cy3 ($\lambda_{em}$=570 nm). The pH titration curves were obtained by plotting Rat. FRET vs hydronium ions concentration, and fitting the data with the following Langmuir-type equation:

$$RATIOMETRIC\ FRET =$$
$$Rat.FRET_{TRIPLEX} + \left( \frac{[H^+] * (Rat.FRET_{TRIPLEX} - Rat.FRET_{DUPLEX})}{[H^+] * K_A^{app}} \right)$$

Where Rat. FRET$_{TRIPLEX}$ and Rat. FRET$_{DUPLEX}$ represent the FRET signal of the switch in the triplex state (closed) and duplex state (open), respectively and where [H⁺] represents the total concentration of hydrogen ions and $$K_A^{app}$$

is the observed acid constant for the switch.

Microcapsule Fabrication

Commercial 2 μm particles based on polystyrene (PS) (Sigma-Aldrich cat. no. 78452), were used to a silicon dioxide shell by a previously reported co-condensation method (Ref. Ma Xing ACS Nano 2016). Briefly, 250 μL of polystyrene particles (stock solution, 10% solids) were mixed with 0.5 mL of 99% ethanol (Panreac Applichem cat. no. 131086-1214), 0.4 mL of Milli-Q water and 25 μl of ammonium hydroxide (Sigma-Aldrich cat. no. 221228). The mixture was stirred at room temperature (RT) for 5 min. Then, 2.5 μL of 3-aminopropyltriethoxysilane (APTES) 99% (Sigma-Aldrich cat. no. 440140) were added to the solution, which was incubated for 6 h, under stirring and at RT. Next, 7.5 μl of tetraethylorthosilicate (TEOS)>99% (Sigma-Aldrich cat. no. 86578) were added and the resulting mixture was let reacting overnight at RT under magnetic stirring. The resulting microparticles consisting of polystyrene coated with a silicon dioxide shell were washed in ethanol three times, by centrifuging them at 3500 rpm for 3.5 min. Then, the polystyrene core was removing by incubating the particles by performing 4 washes in dimethylformamide (DMF)≥99.8% (Acros Organics cat. no. 423640010) during 15 min. The resulting microcapsules were washed thrice in ethanol and stored at room temperature until their use. To characterize the size and morphology of microcapsules, Scanning Electron Microscopy (SEM) (FEI NOVA Nano-SEM 230) and Transmission Electron Microscopy were performed.

Urease and DNA Nanoswitch Functionalization

Hollow silica microcapsules were functionalized with urease to provide them with self-propulsion. For this, SiO₂ microcapsules were washed thrice with Milli-Q by centrifuguing them at 3500 rpm for 3.5 min. After that, three more washes in Phosphate-buffered saline (PBS, pH=7.4) (Thermo Fischer Scientific cat. no. 70011-036) were performed. Microcapsules were then suspended in a 2.5% (wt) glutaraldehyde solution in PBS (Sigma-Aldrich cat. no. G6257) and left at RT for 3 h under end-to-end mixing. The GA-functionalized particles were washed 3 times in PBS 1× and suspended in a solution containing 200 μg/ml urease from *Canavalia ensiformis* (Jack bean) (Sigma-Aldrich cat. no. U4002), and 1 μM DNA-scaffold, in PBS. The resulting solution was kept under end-to-end mixing for 2 h. Then, three washes were performed in PBS and functionalized particles were kept at 40 C until their use.

Motion Analysis

Micromotors were recorded for 20 s at a 25 frames per second rate under an inverted optical microscope (Leica DMi8) equipped with a 63× water immersion objective and a hammamatsu camera. For each condition, at least 15 particles were recorded.

Micromotors trajectories were analyzed by a custom-made Phyton-based code, which allowed to calculate the MSD and speed of the motors, by applying the following equation:

$$MSD(\Delta t) = <(x_i(t + \Delta t) - x_i(t))^2 > \quad (1)$$

By fitting the MSD to equation 1, the speed was obtained.

Urease Activity Measurement

The enzymatic activity was measured by using the Urease Activity Kit (Sigma-Aldrich), which is based on the Barthelot method, a colorimetric assay to measure ammonia production by urease activity, following manufacturer's instructions. First, the micromotors were incubated with 100 mM urea. Then, at different time points the enzymatic reaction was stopped following the manufacturer's instructions. Subsequently, to avoid the interference of the particles with the measurements, samples were centrifuged for 3.5 min at 3500 rpm. Supernatants from each sample were collected and the absorbance was measured at 670 nm to determine the urease activity.

2.2. Results and Discussion

Figure 5:
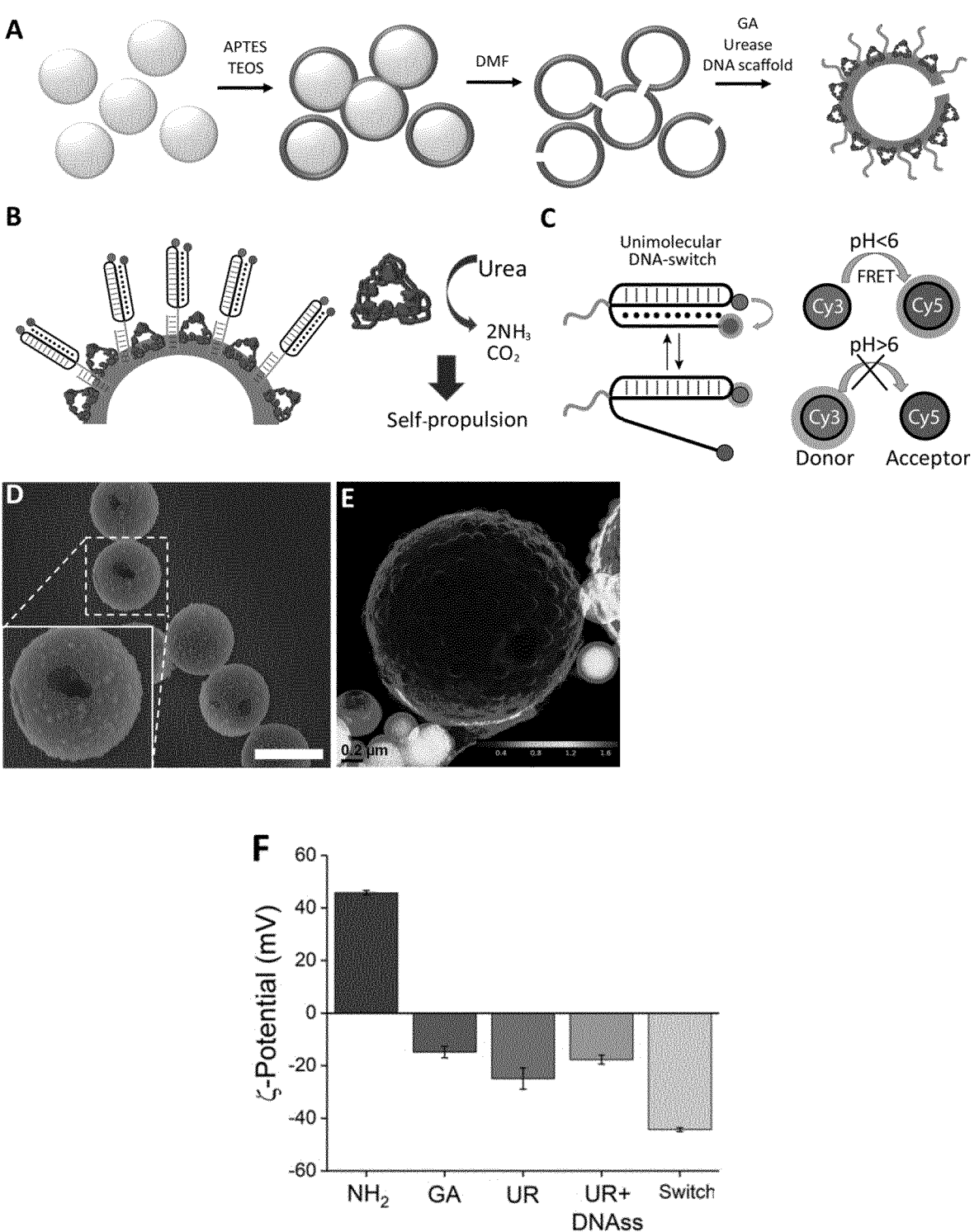
FIG. 5, related to Example 2, shows the fabrication approach and characterization of DNA micromotors. A) Schematic representation of the micromotors fabrication, where a silicon dioxide layer is grown onto a commercial polystyrene template by adding APTES and TEOS silica precursors. The polystyrene core is then removed by DMF and the microcapsules are functionalized with urease and DNA scaffold through the use of glutaraldehyde (GA) linker. B) The pH-responsive DNA nanoswitch hybridizes to the complementary DNA scaffold that is covalently linked on the micromotor. Self-propulsion is achieved by the conversion of urea into ammonia and carbon dioxide, mediated by urease enzyme. C) The pH-dependent triplex-to-duplex transition of the unimolecular DNA nanoswitch results in change of FRET efficiency. D) Scanning electron micrograph of $SiO_2$ microcapsules. Inset shows a magnification of the selected area. Scale bar=2 μm. E) Topographical image obtained by transmission electron microscopy. Calibration bar indicates the height in μm. F) Z-potential measurements of the microparticle surface along the functionalization process ($NH_2$=amine-coated particles resulting from the synthesis; GA=microparticles after incubation with glutaraldehyde, UR=urease-functionalized microparticles; UR+DNAss=microparticles functionalized with both urease and DNA scaffold; Switch=urease and DNA scaffold functionalized microparticles, after their hybridization with the DNA switch for 30 min.)

Hollow silica microcapsules with amine groups on the surface were synthesized according to a previously reported co-condensation method (Ma, X. et al., "Motion Control of Urea-Powered Biocompatible Hollow Microcapsules", *ACS Nano*, 2016, vol. 10(3), pp. 3597-3605), based on the growth of a $SiO_2$ shell onto 2 μm Ø commercial polystyrene microparticles using 3-aminopropyltriethoxysilane (APTES) and tetraethylorthosilicate (TEOS) as silica precursors, followed by the removal of the polystyrene core by dimethylformamide, as depicted in FIG. 5A.

Urease was covalently conjugated to the micromotor surface using Glutaraldehyde (GA) as a linker as described in Example 1. During this step an amino-modified single-stranded DNA (DNAss, 20 bases) was also conjugated, that served as the anchoring moiety for the pH-responsive DNA nanoswitch (FIG. 5B). FIG. 5C shows a schematic representation of the pH sensing strategy based on the open/ closed states of the DNA-nanoswitch, which causes low or high FRET efficiency, respectively. The resulting hollow microcapsules were studied by both scanning and transmission electron microscopy (SEM and TEM, respectively). FIG. 5D shows a SEM micrograph where microcapsules with a very monodispersed size (2.04±0.06 μm, mean±standard error of the mean) and a rough surface can be observed. The microcapsules displayed a hole on their surface, probably due to the proximity of particles during the growth of the silica shell, as reported before, which provides a structural asymmetry. FIG. 5E shows a topographical image obtained by TEM, where the different pseudo-colors indicate the height, in μm.

The functionalization process was characterized by measuring the ζ-potential of microparticles after each step (FIG. 5F). First, the microcapsules displayed a positively charged surface due to the presence of amine groups, which was then shifted to negatively charged due to the modification with GA. After urease addition, surface charges were slightly reduced. The functionalization with both urease and DNAss (UR+DNAss) also resulted in a decrease of ζ-potential with respect to GA.

Figure 6:
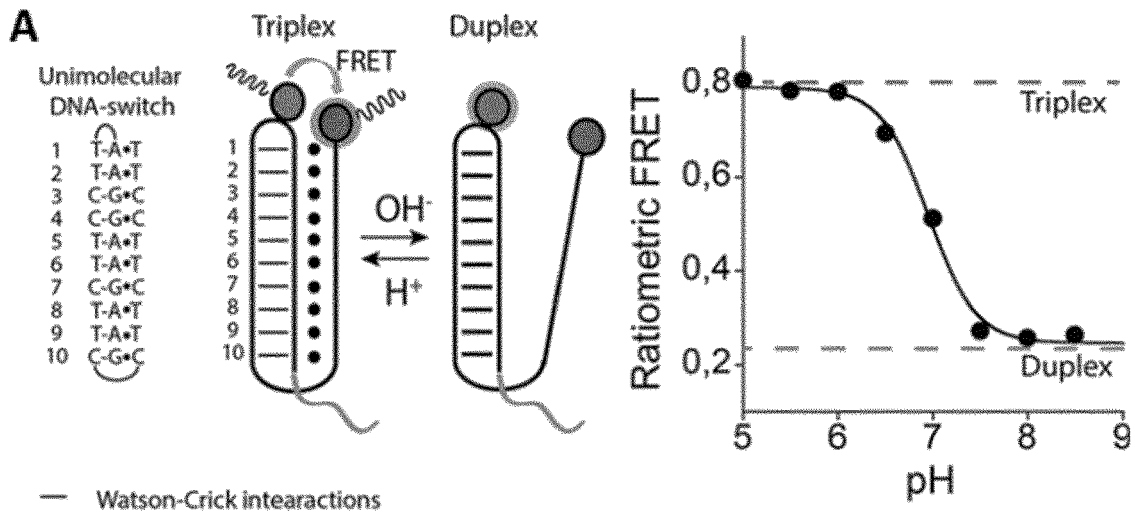
FIG. 6, related to Example 2, shows that triplex-based pH-responsive DNA nanoswitch are able to detect pH changes in solution and conjugated to the micromotor structure. A) Triplex DNA nanoswitch forms an intramolecular double hairpin structure through the formation of pH-insensitive Watson-Crick interactions (dashed line) and pH-sensitive Hoogsteen interactions (dots). Triplex nanoswitch containing CGC and TAT triplets unfolds into a duplex conformation by increasing the pH of the solution. Ratiometric FRET emission (left) showing the triplex-to-duplex transition of the DNA nanoswitch as a function of pH changes in solution. B) CSLM analysis of FRET effect of DNA nanoswitch functionalized microparticles, showing from right to left the Cy3 channel, FRET channel and the FRET/Cy3 ratio value, indicated in the calibration bar. Scale bar=2 μm. The white arrows indicate the functionalized microparticles (originally in red for the Cy3 channel, in green for the FRET channel, and yellow for the Cy3/FRET merge). Quantitative pH measurement by DNA-functionalized micromotors for pH-sensitive (C) and non-pH specific (D), shown as the mean FRET/Cy3 emission values, shown as the mean±standard error of the mean.
Figure 6:
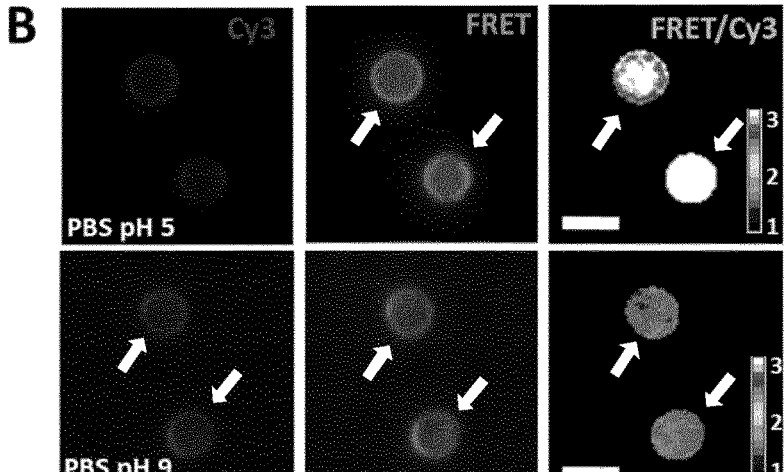
Figure 6:
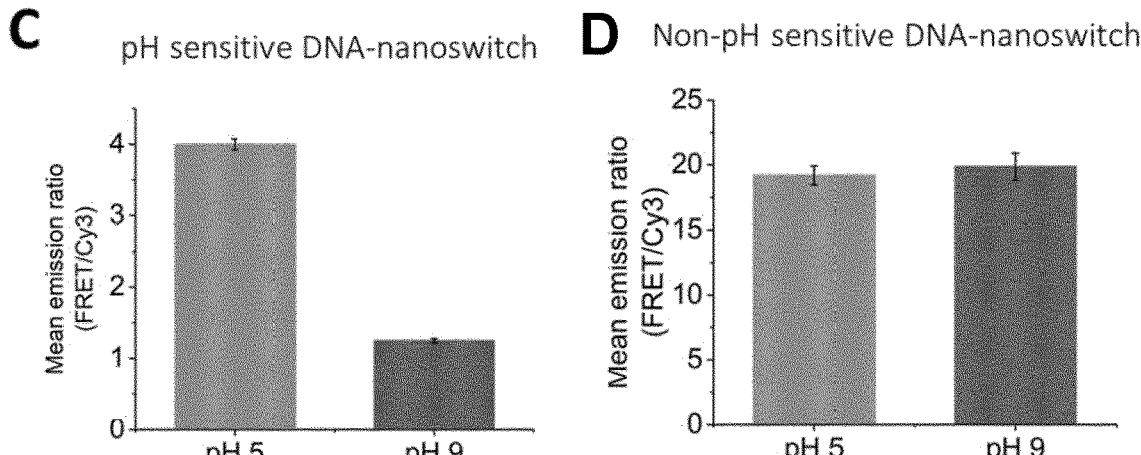

Finally, microparticles were incubated in phosphate buffered saline (PBS) containing the DNA nanoswitch (i.e. 1 μM). A 15-minutes incubation of the nanoswitch with the enzyme/anchoring strand conjugated motors was sufficient to functionalize silica particles with the pH responsive nanoswitch. Of note, the switch presents a 20-bases long flanking tail at the S-end of the sequence complementary with DNAss covalently conjugated onto the silica microcapsule. As a result of the conjugation, a further decrease of the surface charges has been measured and confirms the effective functionalization of the motor with the switch. It is also noteworthy that the pH-responsive DNA nanoswitch here employed is a triplex-forming single stranded DNA containing an intramolecular DNA hairpin stabilized with both Watson-Crick and parallel Hoogsteen interactions. While the Watson-Crick (W-C) interactions are effectively insensitive to pH, the Hoogsteen interactions show strong and programmable pH-dependence (FIG. 6A). By labeling with a FRET pair the nanoswitch we can monitor the pH-dependent triplex to duplex transition which can be used to determine the pH of the solution in the vicinity of the micromotors. More specifically, a Cyanine-3 fluorophore (Cy3) is internally conjugated in the loop of the hairpin duplex DNA and a Cyanine-5 fluorophore (Cy5) is linked at the 3'-end of the triplex-forming DNA portion.

Fluorescence assays performed at a fixed concentration (i.e. 50 nM) of the DNA switch by varying the pH of the buffer solution in a fluorescence microcuvette (100 μL solution) clearly shows changes in the FRET efficiency as a function of pH. As expected, at acidic pH values, the intramolecular triplex structure is favored, and a high FRET efficiency (Cy3 and Cy5 are brought in close proximity) is observed. As the pH of the solution is increased, the triplex structure is destabilized, and a gradual decrease of the FRET signal due to the triplex-to-duplex transition (unfolding) is observed (FIG. 6A). As a note, fluorophores employed here are not sensitive to pH in the range of pHs investigated (from pH 5.0 to pH 9.5) to avoid any interferences in the signal. It is important to note that this class of triplex-based switches show opening/closing kinetics sufficiently fast to allow the real time monitoring of pH variation (average time constant ~100 ms).

To test the functionality of the switch once conjugated to the micromotors, FRET efficiency was monitored through a Leica-SP5 confocal laser scanning microscope (CSLM) equipped with a 63× oil immersion objective (FIG. 6B). For this, micromotors were suspended in PBS either at pH 5 or pH 9 and placed in a 8-well glass bottom dish for their analysis under CSLM. The emission of the donor (Cy3) was recorded using a 564 nm diode laser. The FRET image was obtained by exciting the Cy3 fluorophore and detecting the acceptor (Cy5) emission. Using a custom-made ImageJ plug-in, quantification of the FRET efficiency was achieved by calculating the FRET/Cy3 ratio.

These results indicated that the DNA-nanoswitch modified micromotors were able to detect pH changes in their surrounding environment. To demonstrate the specificity of pH detection and discard any effect of the pH in the fluorescence intensity, the micromotors were modified with a control switch, which did not respond to pH changes. FIGS. 6C and 6D show the quantification of FRET/Cy3 emission from micromotors modified with either a pH responsive DNA-nanoswitch (FIG. 6C) or a non-pH responsive DNA nanoswitch (FIG. 6D). Specifically, as a non-pH responsive probe a single stranded DNA containing the same intramolecular DNA hairpin stabilized through WC-interactions and a scramble DNA tail that does not allow for the triplex folding was selected. As expected, no significant differences were found when using the non-pH responsive nanoswitch presenting high FRET efficiency at all pH evaluated.

The motion dynamics of hollow micromotors double functionalized with urease and DNA-nanoswitch was analyzed by optical recording either in the absence or presence of 100 mM urea acting as fuel. For this, Leica DMi8 inverted fluorescence microscope equipped with a 63× water immersion objective and a Hamamatsu camera was used. At least 15 microparticles per condition were recorded during 20 s at a rate of 25 frames per second (FPS). Using a Python-based code, the trajectories of the micromotors were tracked and, from the trajectories, the MSDs were calculated according to the following equation:

$$MSD(\Delta t) = \langle (x_i(t + \Delta t) - x_i(t))^2 \rangle \qquad (1)$$

where i=2 for 2D analysis. Upon addition of urea substrate, the MSD shows a parabolic shape, which corresponds to a propulsive regime of an active micro-particle.

However, in the absence of fuel, only Brownian motion is observed resulting in a liner fit, indicating that the motion arises from the catalytic reaction on the surface of the micromotors. The speed of propulsive particles was found to be 6.4±0.6 µm/s (mean±standard error of the mean), calculated by applying the following equation:

$$MSD(t) = 4D_t t + v^2, t^2, \qquad (2)$$

where $D_t$=diffusion coefficient, v=velocity and t=time.

Surprisingly, this velocity is comparable to asymmetric Janus enzyme-powered microcapsules reported before (Ma X. et al., supra) and slightly higher than non-Janus microparticles (Patino T. et al., supra). Without being bound by any theory, this effect could be caused by the asymmetry provided by co-immobilizing DNA-nanoswitch and enzymes around the particles in a stochastic fashion.

The capability of micromotors to simultaneously record local pH changes produced while they are self-propelling was assessed by combining both optical tracking and FRET imaging using CSLM, where 25 s videos were recorded at 3FPS. In the absence of fuel, a mean FRET/Cy3 ratio of 1.8±0.09 (mean±standard error of the mean) was observed. When urea was added to the solution, the FRET/Cy3 ratio immediately decreased to 1.5+0.05, indicating a pH increase due to micromotors activity. No significant differences on the FRET/Cy3 ratio were observed during the 25 s of recording. In the absence of fuel, the micromotors only displayed Brownian motion and FRET/Cy3 ratio close to 2. By contrast, in the case of micromotors exposed to urea, the FRET/Cy3 ratio was already decreased at the moment of analysis (0 s), indicating that the pH had already changed as the urease-based enzymatic reaction immediately takes place after adding urea substrate, inducing a local pH change around the particles, which is detected instantaneously.

These results demonstrate the capabilities of active DNA-modified micromotors to sense the microenvironment around them while producing a continuous chemical reaction for self-propulsion.

To gain insights into the instantaneous pH change around the micromotors from the initial moment of the reaction, micromotors were immobilized onto a glass surface using APTES as a coating agent to provide positive surface charges and stabilize the electrostatic interactions with the negatively charged micromotors. Immobilizing micromotors allowed to visualize the same micromotors prior and after the addition of fuel, as well as the analysis at longer time periods (2 min and 10 min) before they would leave out the region of interest.

Figure 7:
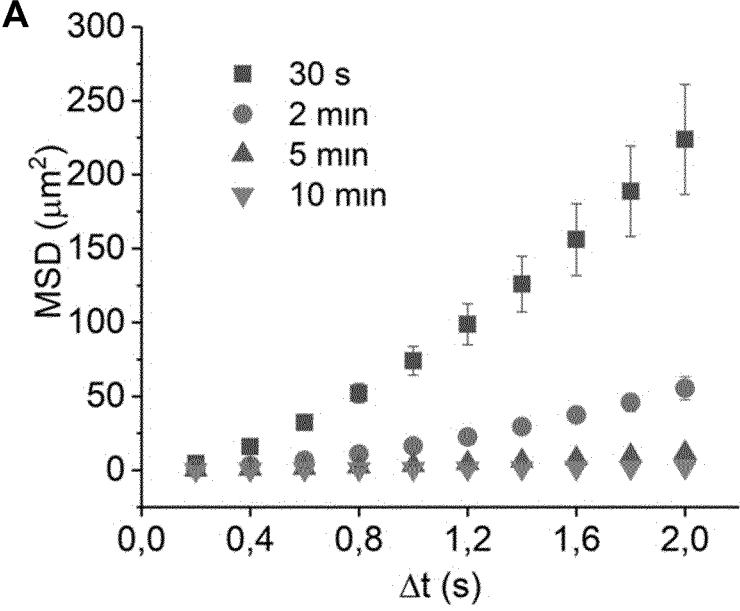
FIG. 7, related to Example 2. A) MSDs of DNA-switch micromotors. Results are shown as the mean±standard error of the mean. B) Speed calculated from the MSDs. Results are shown as the mean±standard error of the mean.
Figure 7:
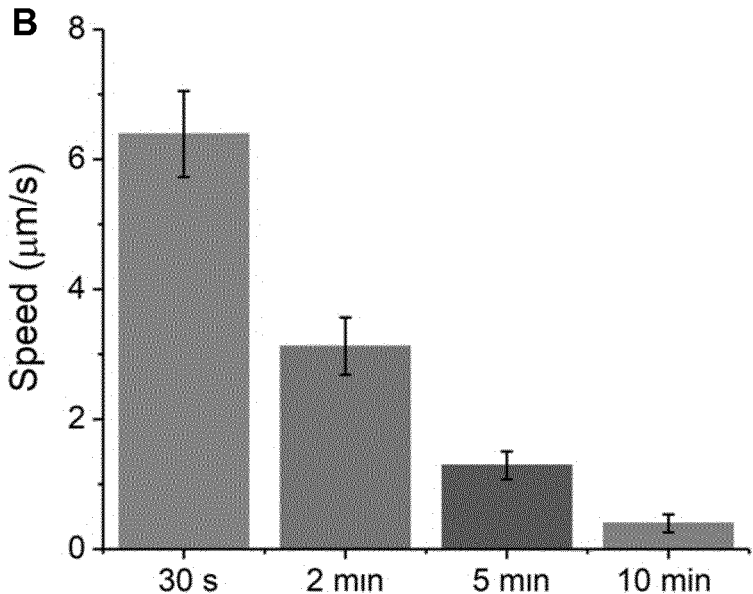

FIGS. 7A and 7B show the average MSD and speed, respectively, obtained from the optical tracking of the motors. A continuous decrease of the MSD and speed can be clearly observed. Interestingly, while the speed decreased over time, the pH continued raising up to 10 min., when the speed was found to be close to 0.

These results suggest that the decrease in speed was not directly attributed to a decrease in enzyme activity and other factors such as the generation of ionic products upon urea decomposition or the high pH not ideal for the enzymatic reaction could be affecting the motion dynamics.

The use of DNA-switch nanotechnology allows the sensing of pH in the microenvironment of the motors and also can be used to monitor their own activity when using enzymes that induce pH changes such as urease. Thus, the integration of biosensing tools into enzyme-powered motors provides new insights to not only their application as sensors but also to monitor their intrinsic activity of the micromotors to understand their motion dynamics and mechanism. In addition, the high versatility of DNA and enzymes allows the tunning of micromotors properties for a wide range of applications.

2.3. Conclusions

The data herein provided demonstrates the potential of combining DNA technology with biocatalytic microswimmers to generate active and smart systems able to simultaneously self-propel while detecting their surrounding environment. Precise and quantitative analysis of pH changes around the surface of micromotors upon their activation in the presence of fuel were achieved through the use of a pH sensitive DNA-nanoswitch and FRET imaging by confocal microscopy. The local pH changes and motion dynamics of micromotors were simultaneously analyzed in the presence of fuel at 30 s, 2 min. and 10 min. The pH continuously increased while the speed was exponentially reduced, indicating that other factors rather than enzyme activity could be affecting the self-propulsion of micromotors.

These results highlight the relevance of simultaneous sensing by micromotors in a precise and quantitative manner not only to monitor microenvironment changes but also as an activity indicator. Future directions will lead to the detection of intracellular or localized tissue changes in pH, and other analytes. Further, this synergistic technology will open the field to multifunctional micromotors where pH changes will trigger the release of cargoes by sense-act platforms.

CITATION LIST

Patino T. et al., "Influence of Enzyme Quantity and Distribution on the Self-Propulsion of Non-Janus Urease-Powered Micromotors", J. Am. Chem. Soc., 2018, vol. 140 (25), pp. 7896-7903.

Ma, X. et al., "Motion Control of Urea-Powered Biocompatible Hollow Microcapsules", ACS Nano, 2016, vol. 10(3), pp. 3597-3605.

Patton, C. J. et al., "Spectrophotometric and Kinetics Investigation of the Berthelot Reaction for the Determination of Ammonia", Anal. Chem., 1977, vol. 49, pp. 464-469.

Campuzano S. et al., "Motion-driven sensing and biosensing using electrochemically propelled nanomotors", Analyst. 2011, vol. 36(22), pp. 4621-30

Altschul et al., "Basic local alignment search tool", 1990, J. Mol. Biol, v. 215, pages 403-410

Higgins et al., "CLUSTAL V: improved software for multiple sequence alignment", 1992, CABIOS, vol. 8(2), pp. 189-191

Inman et al., "The impact of temperature and urinary constituents on urine viscosity and its relevance to bladder hyperthermia treatment", Int J Hyperthermia, 2013, vol. 29(3), pp. 206-10

Xing M A et al., "Motion Control of Urea-Powered Bio-compatible Hollow Microcapsules", ACS Nano., 2016, vol. 10(3), pp. 3597-605.

Ana C. et al., "Enzyme-Powered Nanobots Enhance Anti-cancer Drug Delivery", Advanced Functional Materials, 2017, vol. 28(25).

6. A nanomotor according to claim 1, wherein the heterologous molecule is selected from the group consisting of a targeting molecule, a labelling molecule, a nanosensor and a molecular gate.

7. A nanomotor according to claim 6, wherein the targeting molecule is an antibody.

The invention claimed is:

1. An enzyme-powered non-Janus nanomotor capable of self-propelling, comprising:
   a particle with a surface;
   a propelling enzyme; and
   a heterologous molecule;
wherein the propelling enzyme and the heterologous molecule are discontinuously attached over the whole surface of the particle, and wherein the particle is spherical.

2. A nanomotor according to claim 1, wherein the particle is a nanoparticle or a microparticle.

3. A nanomotor according to claim 1, wherein the particle is made of a material selected from the group consisting of metal, metal oxide, polymer, lipid, protein, cell membrane, cell body, carbonaceous material, and mixtures thereof.

4. A nanomotor according to claim 1, wherein the particle is made of mesoporous silica.

5. A nanomotor according to claim 1, wherein the enzyme is selected from the group consisting of glucose oxidase, urease, catalase, glutamate oxidase, xanthine oxidase, peroxidase, bilirubin oxidase, lipase, protease, hexokinase, acetylcholine esterase, and trypsin.

8. A nanomotor according to claim 6, wherein the nanosensor is a DNA-nanoswitch.

9. A nanomotor according to claim 1 further comprising a cargo.

10. A nanomotor according to claim 1, further comprising an anticancer drug.

11. A pharmaceutical composition comprising a therapeutically effective amount the nanomotor as defined in claim 1, and a pharmaceutically acceptable excipient and/or carrier.

12. A kit of parts comprising a nanomotor as defined in claim 1 and instructions for its use.

13. A kit of parts comprising the pharmaceutical composition as defined in claim 11, and instructions for its use.

14. A method of treating cancer comprising administering an effective amount of the nanomotor of claim 10 to a subject in need thereof.

15. The method of claim 14, wherein the cancer is bladder cancer.

* * * * *